US008741602B2

(12) United States Patent
Ikushiro et al.

(10) Patent No.: US 8,741,602 B2
(45) Date of Patent: Jun. 3, 2014

(54) METHOD FOR PRODUCING GLUCURONIC ACID CONJUGATE USING *SACCHAROMYCES CEREVISIAE*

(75) Inventors: Shinichi Ikushiro, Toyama (JP); Toshiyuki Sakaki, Toyama (JP); Kaori Yasuda, Toyama (JP)

(73) Assignees: Toyama Prefecture, Toyama (JP); Topu Bio Research Co., Ltd., Toyama (JP)

( * ) Notice: Subject to any disclaimer, the term of this patent is extended or adjusted under 35 U.S.C. 154(b) by 0 days.

(21) Appl. No.: 13/580,316

(22) PCT Filed: Feb. 14, 2011

(86) PCT No.: PCT/JP2011/053016
§ 371 (c)(1),
(2), (4) Date: Nov. 1, 2012

(87) PCT Pub. No.: WO2011/105241
PCT Pub. Date: Sep. 1, 2011

(65) Prior Publication Data
US 2013/0059341 A1    Mar. 7, 2013

(30) Foreign Application Priority Data

Feb. 25, 2010  (JP) .................................. 2010-040150

(51) Int. Cl.
*C12N 15/81* (2006.01)
(52) U.S. Cl.
USPC ...................................... 435/75; 435/254.21
(58) Field of Classification Search
USPC .................................. 435/77, 254.21, 320.1
See application file for complete search history.

(56) References Cited

FOREIGN PATENT DOCUMENTS

| JP | 2007-521792 A | 8/2007 |
| JP | 2009-183283 | 8/2009 |
| WO | WO 2006/093289 | 9/2006 |
| WO | WO 2009/073560 | 6/2009 |
| WO | WO 2010/031875 | 3/2010 |

OTHER PUBLICATIONS

Chica et al., Current Opinion Biotechnol. 2005, 16(4): 378-84.*
Dragan et al., Glucuronide Production by Whole-Cell Biotransformation Using Genetically Engineered Fission Yeast Schizosaccharomyces pombe. Drug metabolism and disposition. 38 (3), 509-515, 2010, published on line on Dec. 11, 2009.*
Bailey et al., "Acyl Glucuronide Reactivity in Perspective: Biological Consequences," *Chemico-Biological Interactions* 145:117-137 (2003).
Drăgan et al., "Glucuronide Production by Whole-Cell Biotransformation Using Genetically Engineered Fission Yeast *Schizosaccharomyces pombe*," *Drug Metabolism and Disposition* 38:509-515 (2010).
Hansen et al., "De Novo Biosynthesis of Vanillin in Fission Yeast (*Schizosaccharomyces pombe*) and Baker's Yeast (*Saccharomyces cerevisiae*)," *Appl. Environ. Microbiol.* 75(9):2765-2774 (2009).
Ikushiro et al, "UDP-glucuronic acid transferase, Recent Progress of Drug Metabolism," *Kanzou* 42: 297-301 (2001). (English Translation Provided).
Ikushiro et al., "Functional co-expression of xenobiotic metabolizing enzymes, rat cytochrome P450 1A1 and UDP-glucuronosyltransferase 1A6, in yeast microsomes," *Biochimica et Biophysica Acta* 1672:86-92 (2004).
Ikushiro et al., "Monospecific Antipeptide Antibodies Against Human Hepatic UDP-Glucuronosyltransferase 1A Subfamily (UGT1A) Isoforms," *Drug Metab. Pharmacokinet.* 21(1):70-74 (2006).
Kiang et al., "UDP-glucuronosyltransferases and clinical drug-drug interactions," *Pharmacology & Therapeutics* 106:97-132 (2005).
Mackenzie et al., "Nomenclature update for the mammalian UDP glycosyltransferase (*UGT*) gene superfamily," *Pharmacogenetics and Genomics* 15(10):677-685 (2005).
Oka et al., "Reconstruction of de novo pathway for synthesis of UDP-glucuronic acid and UDP-xylose from intrinsic UDP-glucose in *Saccharomyces cerevisiae*," *FEBS Journal* 273:2645-2657 (2006).
Sakaki et al., "Organella-targeted Expression of Rat Liver Cytochrome P450c27 in Yeast," *The Journal of Biological Chemistry* 267(23):16497-16502 (1992).
Wixon, "Featured Organism: *Schizosaccharomyces pombe*, the fission yeast," *Comp. Funct. Genom.* 3:194-204 (2002).
International Preliminary Report on Patentability for International Application No. PCT/JP2011/053016, dated Sep. 18, 2012.
International Search Report for International Application No. PCT/JP2011/053016, dated Mar. 15, 2011.
Office Action from Japanese Patent Office for Application No. 2011-028516, dated Jan. 10, 2012.
Office Action from Japan Patent Office for Application No. 2011-028516, dated Aug. 30, 2011.
Office Action from Japan Patent Office for JP 2012-089372, dated Aug. 28, 2012.
Ikushiro et al., "Development of glucuronide preparation system for xenobiotic metabolites using genetically engineered budding yeast," *Drug Metab Rev.* 42 Suppl 1:S61 (Abstract only) (2010).
Iwano et al., "cDNA cloning and expression of a bovine phenol UDP-glucuronosyltransferase, BovUGT1A6," *Life Sci.* 68(18):2131-2139 (2001).

(Continued)

*Primary Examiner* — Anand Desai
*Assistant Examiner* — Rama P Ramanujam
(74) *Attorney, Agent, or Firm* — Clark & Elbing LLP; Todd Armstrong

(57) ABSTRACT

Provided is a new method for producing a glucuronide, having excellent productivity and being replaceable with a method using *Saccharomyces* pombe, and to provide a new means used in this production method. Disclosed are: a transformed *Saccharomyces cerevisiae* wherein a gene coding for a UDP-glucose dehydrogenase and a gene coding for a UDP-glucose transferase are inserted in a manner such that said genes can be expressed; a transformed *Saccharomyces cerevisiae* wherein a gene coding for a cytochrome P450 gene is further inserted in a manner such that said gene can be expressed; and a method for producing a glucuronide that includes culturing transformed *Saccharomyces cerevisiae* in the presence of glucose and a substance to be conjugated, generating the glucuronide of the aforementioned substance to be conjugated.

7 Claims, 17 Drawing Sheets

(56) References Cited

OTHER PUBLICATIONS

Sakaki et al., "Production of glucurono- or sulfo-conjugated metabolites using genetically engineered yeast," 17th International Conference on Cytochrome P450: Biochemistry, Biophysics and Structure Medimond. SRL:57-60 (2011).

Zöllner et al., "Production of human phase 1 and 2 metabolites by whole-cell biotransformation with recombinant microbes," Bioanalysis. 2(7):1277-1290 (2010).

Extended European Search Report for European Patent Application No. 11747205.0, dated Jul. 8, 2013 (6 pages).

Klinghammer et al., "Genome-wide analysis of the UDP-glucose dehydrogenase gene family in Arabidopsis, a key enzyme for matrix polysaccharides in cell walls," J Exp Bot. 58(13):3609-21 (2007).

Kobayashi et al., "Molecular and functional characterization of microsomal UDP-glucuronic acid uptake by members of the nucleotide sugar transporter (NST) family," Biochem J. 400(2):281-9 (2006).

Radominska-Pandya et al., "Structure of UDP-glucuronosyltransferases in membranes," Methods Enzymol. 400:116-47 (2005).

Sridhar et al., "Insights on cytochrome p450 enzymes and inhibitors obtained through QSAR studies," Molecules. 17(8):9283-305 (2012).

Wells et al., "Glucuronidation and the UDP-glucuronosyltransferases in health and disease," Drug Metab Dispos. 32(3):281-90 (2004).

\* cited by examiner

SEQUENCE LISTING

<160> NUMBER OF SEQ ID NOS: 26

<210> SEQ ID NO 1
<211> LENGTH: 26
<212> TYPE: PRT
<213> ORGANISM: Homo sapiens

<400> SEQUENCE: 1

Met Ala Arg Ala Gly Trp Thr Gly Leu Leu Pro Leu Tyr Val Cys Leu
1               5                   10                  15

Leu Leu Thr Cys Gly Phe Ala Lys Ala Gly
            20                  25

```
<210> SEQ ID NO 2
<211> LENGTH: 26
<212> TYPE: PRT
<213> ORGANISM: Homo sapiens

<400> SEQUENCE: 2

Met Ala Cys Leu Leu Arg Ser Phe Gln Arg Ile Ser Ala Gly Val Phe
1               5                   10                  15

Phe Leu Ala Leu Trp Gly Met Val Val Gly
            20                  25

<210> SEQ ID NO 3
<211> LENGTH: 26
<212> TYPE: PRT
<213> ORGANISM: Homo sapiens

<400> SEQUENCE: 3

Met Ala Pro Arg Arg Val Asp Gln Pro Arg Ser Phe Met Cys Val Ser
1               5                   10                  15

Thr Ala Asp Leu Trp Leu Cys Glu Ala Gly
            20                  25

<210> SEQ ID NO 4
<211> LENGTH: 38
<212> TYPE: DNA
<213> ORGANISM: Artificial Sequence
<220> FEATURE:
<223> OTHER INFORMATION: Forward primer

<400> SEQUENCE: 4
cccaagctta aaaatggtg aagatatgct gcatagga                            38

<210> SEQ ID NO 5
<211> LENGTH: 38
<212> TYPE: DNA
<213> ORGANISM: Artificial Sequence
<220> FEATURE:
<223> OTHER INFORMATION: Reverse primer

<400> SEQUENCE: 5
cccaagcttt catgccacag caggcatatc cttgagcc                           38

<210> SEQ ID NO 6
<211> LENGTH: 1443
<212> TYPE: DNA
<213> ORGANISM: Arabidopsis thaliana

<400> SEQUENCE: 6
atggtgaaga tttgctgcat tggagctgga tatgttggtg gtccaaccat ggctgtcatt    60
gctctaaagt gtccatctgt tgaagtagct gttgttgata tctctgtgcc aaggatcaat   120
gcctggaaca gtgatcagtt accgatctat gagcctggtc ttgatgatgt cgttaagcag   180
tgccgtggaa agaatctctt cttcagcacc gatgttgaga acatgtgag agaggctgac    240 attgttttg tgtctgtcaa cacccctact aagacccgtg tcttggagc tgcaaagct     300 gcggatttga cttactggga gagcgctgct cgtatgattg ccgatgtttc ggtttccgac   360
aagattgttg ttgagaaatc aactgttcct gtcaaaaccg cagaggcaat tgagaagatt   420
cttacacaca acagcaaagg aatcaaattc cagattctgt caaaccctga gttccttgct   480
gaaggaaccg ctattgaaga ccttttcatg cctgaccgtg tcctcatcgg tggtcgtgaa   540
acaactgaag gctttgcagc cgtcaaagcc ttgaaagaca tttatgccca atgggtccct   600
```

```
gaagagagaa tcctcaccac caatctatgg tctgccgagc tttccaagct tgcagctaat    660
gccttcctag cccagagaat ctcatcagtc aatgcaatgt ccgctctctg tgaggcaact    720
ggcgccaatg tctcagaggt ctcttatgct gtgggcaaag actctcgtat tggtcccaag    780
ttcttgaact ctagtgttgg gttcggagga tcttgtttcc agaaagatat tctcaactta    840
gtctacatct gcgaatgcaa cggcttaccc gaagttgctg agtactggaa acaagtcatc    900
aagatcaacg actaccagaa aacccgattt gttaaccgca ttgtctcttc aatgtttaac    960
acagtctcca caaaaagat tgcggttctc ggcttcgctt tcaagaaaga cactggagac   1020
actagagaga ctccagccat tgatgtctgc aaaggtctgt taggtgacaa ggctcgtctc   1080
agcatctacg acccacaagt cactgaagag cagatccaaa gagacttaac catgaacaaa   1140
ttcgactggg accacccact tcatctccag cccatgagcc ccaccactgt gaagcaagtc   1200
tcagtcgctt gggacgcata cactgcaacc aaagacgccc acggtatctg cattttaacc   1260
gagtgggacg agttcaagaa acttgatttc cagcggatct tgagaatat gcagaaaccg   1320 gcttttgttt ttgacggtag aaacgtggtc gacgctgata aactcaggga gattgggttt   1380
attgtttact ccattggtaa gccattggac cagtggctca aggacatgcc tgctcttgcc   1440
taa                                                                 1443
```

```
<210> SEQ ID NO 7
<211> LENGTH: 38
<212> TYPE: DNA
<213> ORGANISM: Artificial Sequence
<220> FEATURE:
<223> OTHER INFORMATION: Forward primer

<400> SEQUENCE: 7
cccaagctta aaaatggtt gagatcaaga agatctgt                             38

<210> SEQ ID NO 8
<211> LENGTH: 38
<212> TYPE: DNA
<213> ORGANISM: Artificial Sequence
<220> FEATURE:
<223> OTHER INFORMATION: Reverse primer

<400> SEQUENCE: 8
cccaagcttc tagactttgg gcttcttgtt aggtggat                             38

<210> SEQ ID NO 9
<211> LENGTH: 1482
<212> TYPE: DNA
<213> ORGANISM: Rat

<400> SEQUENCE: 9
atggttgaga tcaagaagat ctgttgcatt ggtgcgggct acgtcggcgg acccacatgc     60
agtgtcattg ctcgcatgtg ccctgaaatc agggtaacgg ttgtggatgt caatgaggcc    120
aggatcaatg catggaattc tccaacgctt cctatttatg agcctggact aaaagaagta    180
gtcgaatcct gtcgagggaa aaacctcttt ttttctacca atattgatga tgccatcaga    240
gaagccgatc tagtgtttat ttctgtgaac acaccaacaa aaacatatgg aatgggaaaa    300
ggccgggcgg cagatctgaa gtatatcgaa gcttgtgctc gccgcattgt gcagaactca    360
aatgggtaca aaattgtgac tgagaaaagc acagtccctg tgcgggcagc ggaaagcatc    420
cgccgcatat ttgatgccaa cacaaagccc aacttgaatc tacaggttct gtccaatcct    480
gagttcttgg cagagggaac agccatcaag gacctaaaga acccagacag agtcctgatt    540
```

```
ggaggggatg agaccccaga gggccagaga gctgttcagg cactctgtgc tgtgtacgag      600
cactgggttc ccaaggaaaa gatcctcacc accaacactt ggtcctcaga gctttccaaa      660
ctggcagcca atgctttct tgcccagagg atcagcagca ttaactccat aagtgctctg       720
tgtgaaagca caggcgccga tgtggaagag gtggcaacgg ctatcgggat ggaccaaaga      780
attggaaata agtttctaaa agccagcgtt ggttttggtg ggggctgctt ccaaaaagat      840
gttctgaatt tggtttatct ctgtgaggct ctgaatctgc ccgaagtagc tcgttactgg      900
cagcaggtca tagacatgaa tgactaccag aggaggaggt ttgcatcacg gatcatagac      960
agcctgttta atacagtgac tgataagaag atagctatct tggggtttgc gttcaaaaag     1020
gatactggtg ataccaggga gtcctccagt atctacatta gcaaatacct gatggacgag     1080
ggtgcgcacc tccacatcta cgaccccaaa gtacccaggg agcagatagt ggtggatctt     1140
tctcatccag gcgtctcagc ggatgaccaa gtgtccagac tggtgaccat ttccaaggat     1200
ccatatgaag catgtgatgg cgcccatgcc ctcgttatct gcacagagtg ggacatgttt     1260
aaggaactgg attatgaacg gattcataaa agaatgctga agccagcctt catatttgat     1320
ggccggcgtg tcctggatgg gctccacaat gagctacaga ccattggctt ccagattgaa     1380
acaattggca aaaaggtatc ttccaagaga attccataca ctcctggtga aattccaaag     1440
tttagtcttc aggatccacc taacaagaag cccaaagtct ag                       1482
```

<210> SEQ ID NO 10  
<211> LENGTH: 27  
<212> TYPE: DNA  
<213> ORGANISM: Artificial Sequence  
<220> FEATURE:  
<223> OTHER INFORMATION: YGAP-P primer

<400> SEQUENCE: 10
aatgacaccg tgtggtgatc ttcaagg                                           27

<210> SEQ ID NO 11  
<211> LENGTH: 35  
<212> TYPE: DNA  
<213> ORGANISM: Artificial Sequence  
<220> FEATURE:  
<223> OTHER INFORMATION: Forward primer

<400> SEQUENCE: 11
gttgaagctt gcatggataa gaatgcagaa agccc                                  35

<210> SEQ ID NO 12  
<211> LENGTH: 35  
<212> TYPE: DNA  
<213> ORGANISM: Artificial Sequence  
<220> FEATURE:  
<223> OTHER INFORMATION: Reverse primer

<400> SEQUENCE: 12
acggccagtg aattcgcggc cgcgatccgg gcgtc                                  35

<210> SEQ ID NO 13  
<211> LENGTH: 35  
<212> TYPE: DNA  
<213> ORGANISM: Artificial Sequence  
<220> FEATURE:  
<223> OTHER INFORMATION: Forward primer

<400> SEQUENCE: 13
gaattcactg gccgtcgttt tacaacgtcg tgact                                  35

```
<210> SEQ ID NO 14
<211> LENGTH: 35
<212> TYPE: DNA
<213> ORGANISM: Artificial Sequence
<220> FEATURE:
<223> OTHER INFORMATION: Reverse primer

<400> SEQUENCE: 14
catgcaagct tcaacagagg aaagaataac gcaaa                                    35

<210> SEQ ID NO 15
<211> LENGTH: 72
<212> TYPE: DNA
<213> ORGANISM: Homo sapiens

<400> SEQUENCE: 15
atggctcgtg cagggtggac tggcctcctt cccctatatg tgtgtctact gctgacctgt         60
ggctttgcca ag                                                             72

<210> SEQ ID NO 16
<211> LENGTH: 72
<212> TYPE: DNA
<213> ORGANISM: Homo sapiens

<400> SEQUENCE: 16
atggctgtgg agtcccaggg cggacgccca cttgtcctgg cctgctgct gtgtgtgctg          60 ggcccagtgg tg                                                             72

<210> SEQ ID NO 17
<211> LENGTH: 78
<212> TYPE: DNA
<213> ORGANISM: Homo sapiens

<400> SEQUENCE: 17
atggcttgca cagggtggac cagccccctt cctctatgtg tgtgtctgct gctgacctgt         60
ggctttgccg aggcaggg                                                       78

<210> SEQ ID NO 18
<211> LENGTH: 105
<212> TYPE: DNA
<213> ORGANISM: Artificial Sequence
<220> FEATURE:
<223> OTHER INFORMATION: PCR  primer

<400> SEQUENCE: 18
cccaagctta aaaaaatggc tcgtgcaggg tggactggcc tccttcccct atatgtgtgt         60
ctactgctga cctgtggctt tgccaaggct gggaagatac tgttg                        105

<210> SEQ ID NO 19
<211> LENGTH: 105
<212> TYPE: DNA
<213> ORGANISM: Artificial Sequence
<220> FEATURE:
<223> OTHER INFORMATION: PCR primer

<400> SEQUENCE: 19
cccaagctta aaaaaatggc tcgtgcaggg tggactggcc tccttcccct atatgtgtgt         60
ctactgctga cctgtggctt tgccaaggca gggaagctac tggta                        105

<210> SEQ ID NO 20
<211> LENGTH: 45
<212> TYPE: DNA
```

```
<213> ORGANISM: Artificial Sequence
<220> FEATURE:
<223> OTHER INFORMATION: Reverse primer

<400> SEQUENCE: 20
cccaagcttg atatcttctc aatgggtctt ggatttgtgg gcttt          45

<210> SEQ ID NO 21
<211> LENGTH: 30
<212> TYPE: DNA
<213> ORGANISM: Artificial Sequence
<220> FEATURE:
<223> OTHER INFORMATION: Forward primer

<400> SEQUENCE: 21
ttgcggccgc tctaactgat ctatccaaaa                            30

<210> SEQ ID NO 22
<211> LENGTH: 29
<212> TYPE: DNA
<213> ORGANISM: Artificial Sequence
<220> FEATURE:
<223> OTHER INFORMATION: Reverse primer

<400> SEQUENCE: 22
cccaagcttt gttttatatt tgttgtaaa                             29

<210> SEQ ID NO 23
<211> LENGTH: 29
<212> TYPE: DNA
<213> ORGANISM: Artificial Sequence
<220> FEATURE:
<223> OTHER INFORMATION: Forward primer

<400> SEQUENCE: 23
cccaagctta ttgaattgaa ttgaaatcg                             29

<210> SEQ ID NO 24
<211> LENGTH: 28
<212> TYPE: DNA
<213> ORGANISM: Artificial Sequence
<220> FEATURE:
<223> OTHER INFORMATION: Reverse primer

<400> SEQUENCE: 24
ttgcggccgc taacgaacgc agaatttt                              28

<210> SEQ ID NO 25
<211> LENGTH: 1480
<212> TYPE: DNA
<213> ORGANISM: Saccharomyces cerevisiae

<400> SEQUENCE: 25
tctaactgat ctatccaaaa ctgaaaatta cattcttgat taggtttatc acaggcaaat     60
gtaatttgtg gtattttgcc gttcaaaatc tgtagaattt tctcattggt cacattacaa    120
cctgaaaata ctttatctac aatcatacca ttcttataac atgtcccctt aatactagga    180
tcaggcatga acgcatcaca gacaaaatct tcttgacaaa cgtcacaatt gatccctccc    240
catccgttat cacaatgaca ggtgtcattt tgtgctctta tgggacgatc cttattaccg    300
cttcatccg gtgatagacc gccacagagg ggcagagagc aatcatcacc tgcaaaccct    360
tctatacact cacatctacc agtgtacgaa ttgcattcag aaaactgttt gcattcaaaa    420
ataggtagca tacaattaaa acatggcggg catgtatcat tgcccttatc ttgtgcagtt    480
```

```
agacgcgaat ttttcgaaga agtaccttca aagaatgggg tcttatcttg ttttgcaagt        540
accactgagc aggataataa tagaaatgat aatatactat agtagagata acgtcgatga        600
cttcccatac tgtaattgct tttagttgtg tattttagt gtgcaagttt ctgtaaatcg         660 attaatttt ttttctttcc tcttttatt aaccttaatt tttattttag attcctgact          720
tcaactcaag acgcacagat attataacat ctgcataata ggcatttgca agaattactc        780
gtgagtaagg aaagagtgag gaactatcgc ataccctgcat ttaaagatgc cgatttgggc       840
gcgaatcctt tattttggct tcaccctcat actattatca gggccagaaa aaggaagtgt        900
ttccctcctt cttgaattga tgttaccctc ataaagcacg tggcctctta tcgagaaaga       960
aattaccgtc gctcgtgatt tgtttgcaaa aagaacaaaa ctgaaaaaac ccagacacgc       1020
tcgacttcct gtcttcctat tgattgcagc ttccaatttc gtcacacaac aaggtcctag       1080
cgacggctca caggttttgt aacaagcaat cgaaggttct ggaatggcgg gaaagggttt      1140
agtaccacat gctatgatgc ccactgtgat ctccagagca aagttcgttc gatcgtactg      1200
ttactctctc tctttcaaac agaattgtcc gaatcgtgtg acaacaacag cctgttctca      1260
cacactcttt tcttctaacc aagggggtgg tttagtttag tagaacctcg tgaaacttac      1320
atttacatat atataaactt gcataaattg gtcaatgcaa gaaatacata tttggtcttt      1380
tctaattcgt agtttttcaa gttcttagat gctttctttt tctctttttt acagatcatc      1440
aaggaagtaa ttatctactt tttacaacaa atataaaaca                            1480

<210> SEQ ID NO 26
<211> LENGTH: 276
<212> TYPE: DNA
<213> ORGANISM: Saccharomyces cerevisiae

<400> SEQUENCE: 26
attgaattga attgaaatcg atagatcaat ttttttcttt tctctttccc catcctttac         60
gctaaaataa tagtttattt tatttttga atatttttta tttatatacg tatatataga         120
ctattattta tcttttaatg attattaaga tttttattaa aaaaaaattc gctcctcttt        180
taatgccttt atgcagtttt tttttcccat tcgatatttc tatgttcggg ttcagcgtat        240
tttaagttta ataactcgaa aattctgcgt tcgtta                                 276
```

METHOD FOR PRODUCING GLUCURONIC ACID CONJUGATE USING *SACCHAROMYCES CEREVISIAE*

CROSS-REFERENCE TO RELATED APPLICATIONS

This application is the U.S. National Stage filing under 35 U.S.C. §371 of International Application No. PCT/JP2011/053016, filed Feb. 14, 2011, which claims benefit of Japanese Patent Application No. JP 2010-040150, filed Feb. 25, 2010.

TECHNICAL FIELD

The present invention relates to a method for producing a glucuronide, and to a *Saccharomyces cerevisiae* expression vector and transformant employed therein. The *Saccharomyces cerevisiae* expression vector is one into which UDP-glucuronosyl transferase and/or UDP-glucose dehydrogenase has been introduced. The transformant is *Saccharomyces cerevisiae* that has been transformed with the *Saccharomyces cerevisiae* expression vector.

BACKGROUND ART

The analysis of pharmaceutical metabolites within the human body is important in the development of pharmaceuticals. Glucuronides are eliminated as detoxifying metabolites of pharmaceuticals. However, the possibility that some could turn into reactive metabolites and exhibit toxicity has been pointed out. For example, among the glucuronides, acyl glucuronides, which are ester glucuronides, present the possibility of becoming reactive metabolites and causing drug-induced liver damage (Nonpatent Reference 1).

Accordingly, while it is necessary to evaluate the safety of the glucuronides themselves, site-specific glucuronidation is extremely difficult by organic synthesis methods. Accordingly, there is great need for a method permitting the efficient producing of a targeted glucuronide using enzymes, microorganisms, and the like. Currently, the preparation of glucuronides using animal liver-derived microsome fractions is being practiced. However, the productivity and the scope of applicability are inadequate. Human glucuronosyl transferase employing an insect cell system is already commercially available. However, use as an enzyme source in the preparation of glucuronides is impractical from a cost perspective.

The present inventors constructed the expression system of glucuronosyl transferase employing *Saccharomyces cerevisiae* that has been employed thus far, and proposed the enzymatic synthesis of glucuronides that are pharmaceutical metabolites employing it as an enzyme source for glucuronide preparation (Nonpatent Reference 2).

Recently, Dragan et al. (Nonpatent Reference 7, Patent Reference 1) constructed a system producing glucuronides from *Schizosaccharomyces pombe* (*S. Pombe*) cells expressing UGT employing *S. Pombe*.

CITATION LIST

Patent References

Patent Reference 1: WO2010/031875

Nonpatent References

Nonpatent Reference 1: Bailey M J, Dickinson R G. Acyl glucuronide reactivity in perspective: biological consequences. Chem Biol Interact. 145, 117-37. (2003)

Nonpatent Reference 2: S. Ikushiro, M. Sahara, Y. Emi, Y. Yabusaki, T. Iyanogi: Functional co-expression of xenobiotic metabolizing enzymes, rat cytochrome P450 1A1 and UDP-glucuronosylransferase 1A6. Biochimica et Biophysica Acta 1672 (2004) 86-92

Nonpatent Reference 3: Mackenzie, P. I, Walter Bock, K., Burchell, B., Guillemette, C., Ikushiro, S. I., Iyanagi, T., Miners, J. O., Owens, I. S. and Nebert, D. W.: Nomenclature Update for the Mammalian UDP Glycosyltransferase (UGT) Gene Superfamily. Pharmacogenetics and Genomics, 10, 677-685 (2005)

Nonpatent Reference 4: Sinichi Ikushiro, Yoshikazu Ebi, Yutaka Iyanagi, UDP-glucuronic acid transferase, Recent Progess of Drug Metabolism, Kanzou, 42, pp. 297-301 (2001)

Nonpatent Reference 5: T. Sakaki, M. Akiyoshi-Shibata, Y. Yabusaki, H. Ohkawa, Organella targeted expression of rat liver cytochrome P450c27 in yeast: genetically engineered alteration of mitochondrial P450 into a microsomal form creates a novel functional electron transport chain, J. Biol. Chem. 267 16497-16502. (1992)

Nonpatent Reference 6: Ikushiro. S., Emi, Y., Kato, Y., Yamada, S, and Sakaki, T.: Monospecific antipeptide antibodies against human hepatic UDP-glucuronosyltransferase 1A subfamily (UGT1A) isoforms. Drug Metabolism and Pharmacokinetics, 21, 70-75 (2006)

Nonpatent Reference 7: Dragan C A, Buchheit D, Bischoff D, Ebner T, Bureik M.: Glucuronide production by whole-cell biotransformation using genetically engineered fission yeast *S. pombe*. Drug Metab Dispos. 38 509-515. (2010)

Nonpatent Reference 8: Jo Wixon: Featured Organism: *Schizosaccharomyces pombe*, the fission yeast. Comp Funct Genom, 3: 194-204 (2002)

Nonpatent Reference 9: Esben H. Hansen, Birger Lindberg Møller, Gertrud R. Kock, Camilla M. Bunner, Charlotte Kristensen, Ole R. Jensen, Finn T. Okkels, Carl E. Olsen, Mohammed S. Motawia, and Jørgen Hansen1: De Novo Biosynthesis of Vanillin in Fission Yeast (*Schizosaccharomyces pombe*) and Baker's Yeast (*Saccharomyces cerevisiae*) APPLIED AND ENVIRONMENTAL MICROBIOLOGY, 75, 2765-2774 (2009)

Nonpatent Reference 10: Tony K. L. Kiang, Mary H. H. Ensom, Thomas K. H. Chang: UDP-glucuronosyltransferases and clinical drug-drug interactions. Pharmacology & Therapeutics 106 97-132 (2005)

Nonpatent Reference 11: Ikushiro, S., Sahara, M., Emi, Y., Yabusaki, Y., and Iyanagi, T.: Functional Coexpression of Xenobiotic Metabolizing Enzymes, Rat Cytochrome P4501A1 and UDP-Glucuronosyltransferase 1A6, in Yeast Microsomes. Biochimica Biophysica Acta, 1672, 86-92 (2004)

The entire contents of Patent Reference 1 and Nonpatent References 1 and 11 are incorporated herein particularly by reference.

SUMMARY OF INVENTION

Problem to Be Solved by the Invention

However, the method of preparing glucuronides by enzymatic conversion in vitro with human-derived UDP-glucuronosyl transferase (UGT) obtained by expression in yeast as the enzyme source is inadequate in terms of productivity and scope of applicability. In particular, the UDP-glucuronic acid that is employed as the glycosyl donor is expensive. The discovery of a method that can lower the cost when preparing glucuronides is being awaited.

The system employing *S. Pombe* described in Nonpatent Reference 7 affords overall low productivity and remains impractical.

Accordingly, the object of the present invention is to provide a new method for producing glucuronides that affords good productivity in contrast to the above methods, and a new means employed in this producing method.

Means of Solving the Problem

Accordingly, the present inventors planned to employ *Saccharomyces cerevisiae* (*S. cerevisiae*) as host and to change the metabolic system of *S. cerevisiae* expressing UGT to permit the production of a sugar donor in the form of UDP-glucuronic acid. However, *S. cerevisiae* lacks the ability to produce UDP-glucuronic acid, which is considered essential to glucuronide production. Thus, the direct conversion into glucuronide within the cells was impossible. Accordingly, to impart the ability to produce UDP-glucuronic acid to *S. cerevisiae*, a UDP-glucose dehydrogenase gene derived from another organism was introduced. As a result, the expression of UDP-glucuronic acid was observed in *S. cerevisiae*. The *S. cerevisiae* into which UDPGDH had been incorporated was caused to simultaneously express UGT molecular species, thereby achieving at high yield the direct conversion into glucuronide of the substrate added to *S. cerevisiae*. In this manner the present inventors employed *S. cerevisiae* as host to successfully construct a glucuronide conversion system in which the ability to produce glucuronide was greatly enhanced in *S. cerevisiae*.

*S. cerevisiae* and *S. Pombe* are classified as yeasts. They are thought to have branched off some 3 to 4 hundred million years ago. The difference between the two as species can be said to be comparable to the difference between *S. Pombe* and animals (Nonpatent Reference 8). Both have similar genome sizes (*S. cerevisiae*: 12 Mb, *S. Pombe*: 14 Mb) and numbers of genes (*S. cerevisiae*: about 7,000; *S. Pombe* about 5,000). However, marked differences in numbers of chromosomes (as haploids, *S. cerevisiae*: 17, *S. Pombe*: 3) and growth methods (*S. cerevisiae* buds and *S. Pombe* fissile) are seen. There is also little homology between individual genes. Still further, the situations when expressing heterogeneous proteins derived from mammals are quite different. Although high expression is achieved in *S. Pombe*, high expression is not necessarily achieved in *S. cerevisiae* (Nonpatent Reference 9). Due to this situation, as described in Nonpatent Reference 7, although the simultaneous expression of UDPGDH and UGT has been successfully achieved in *S. Pombe*, the simultaneous expression of UDPGDH and UGT when applied as is to *S. cerevisiae* does not necessarily work.

The present invention is as follows:

[1]
*Saccharomyces cerevisiae* that has been transformed by the insertion in an expressible manner of a gene coding for UDP-glucose dehydrogenase and a gene coding for UDP-glucuronosyl transferase.

[2]
The *Saccharomyces cerevisiae* according to [1], that has been further transformed by inserting in an expressible manner a gene coding for cytochrome P450.

[3]
A transformed *Saccharomyces cerevisiae* selected from the group consisting of (A) to (G) below:
(A) *Saccharomyces cerevisiae* that has been transformed with a UDP-glucose dehydrogenase expression vector and a UDP-glucuronosyl transferase expression vector;
(B) *Saccharomyces cerevisiae* that has been transformed with a UDP-glucuronosyl transferase and UDP-glucose dehydrogenase expression vector;
(C) *Saccharomyces cerevisiae* that has been transformed with a UDP-glucose dehydrogenase expression vector, a UDP-glucuronosyl transferase expression vector, and a cytochrome P450 gene expression vector;
(D) *Saccharomyces cerevisiae* that has been transformed with a UDP-glucuronosyl transferase and UDP-glucose dehydrogenase expression vector, and a cytochrome P450 gene expression vector;
(E) *Saccharomyces cerevisiae* that has been transformed with a UDP-glucuronosyl transferase expression vector and a UDP-glucose dehydrogenase and cytochrome P450 gene expression vector;
(F) *Saccharomyces cerevisiae* that has been transformed with a UDP-glucuronosyl transferase and cytochrome P450 gene expression vector and a UDP-glucose dehydrogenase expression vector; and
(G) *Saccharomyces cerevisiae* that has been transformed with a UDP-glucose dehydrogenase, UDP-glucuronosyl transferase, and cytochrome P450 gene expression vector.

[4]
The transformed *Saccharomyces cerevisiae* according to [3], wherein the UDP-glucose dehydrogenase expression vector is comprised of a UDP-glucose dehydrogenase gene that has been inserted in an expressible manner into a *Saccharomyces cerevisiae* expression vector;
the UDP-glucuronosyl transferase expression vector is comprised of a UDP-glucuronosyl transferase gene that has been inserted in an expressible manner into a *Saccharomyces cerevisiae* expression vector; and
the UDP-glucuronosyl transferase and UDP-glucose dehydrogenase expression vector is comprised of a UDP-glucuronosyl transferase gene and a UDP-glucose dehydrogenase gene that have been inserted in an expressible manner into a *Saccharomyces cerevisiae* expression vector;

[5]
The transformed *Saccharomyces cerevisiae* according to [4], wherein the *Saccharomyces cerevisiae* expression vector is an autonomous replication vector or a chromosome integrative vector.

[6]
The transformed *Saccharomyces cerevisiae* of any one of [1], [2], and [4] to [5], wherein the UDP-glucose dehydrogenase gene is a gene derived from an animal or a plant.

[7]
The transformed *Saccharomyces cerevisiae* of any one of [1], [2], and [4] to [5], wherein the UDP-glucose dehydrogenase gene is a gene derived from *Arabidopsis* or a gene derived from a rat.

[8]
The transformed *Saccharomyces cerevisiae* of any one of [1], [2], and [4] to [7], wherein the UDP-glucuronosyl transferase gene is a gene derived from a mammal.

[9]
The transformed *Saccharomyces cerevisiae* of any one of [1], [2], and [4] to [7], wherein the UDP-glucuronosyl transferase gene is a human-derived gene.

[10]
The transformed *Saccharomyces cerevisiae* of any one of [3] to [9], wherein the cytochrome P450 gene expression vector is comprised of a cytochrome P450 gene that has been inserted in an expressible manner in a *Saccharomyces cerevisiae* expression vector.

[11]
The transformed *Saccharomyces cerevisiae* according to any one of [1] to [10] wherein, when the UDP-glucuronosyl transferase gene in the UDP-glucuronosyl transferase expression vector is a low-expression level glucuronosyl transferase gene with an expression level of 50% or less that of UGT1A7, either the signal sequence gene of the low-expression level glucuronosyl transferase gene is substituted with the signal sequence gene of a high-expression level glucuronosyl transferase with an expression level of 80% or more of UGT1A7, or
the signal sequence gene is (A) a gene coding for any one of amino acid sequences (a) to (c) indicated below; (B) a gene coding for an amino acid sequence comprising any one of amino acid sequences (a) to (c) in which 1 to 5 amino acids have been substituted or deleted; or (C) a gene coding for an amino acid sequence comprising any one of amino acid sequences (a) to (c) to which 1 to 5 amino acids have been added, such that when the gene coding for the amino acid sequence with substitutions or deletions of (B) or the amino acid sequence with additions of (C) is employed as a signal sequence gene, the expression level of glucuronosyl transferase is 80% or more that of the wild strain:

(a)
(SEQ. ID NO. 1)
MARAGWTGLLPLYVCLLLTCGFAKAG, (b)
(SEQ. ID NO. 2)
MACLLRSFQRISAGVFFLALWGMVVG, (c)
(SEQ. ID NO. 3)
MAPRRVDQPRSFMCVSTADLWLCEAG.

[12]
The transformed *Saccharomyces cerevisiae* according to [11], wherein the low-expression level glucuronosyl transferase is UGT1A1, UGT1A4, UGT1A8, or UGT1A9.
[13]
The transformed *Saccharomyces cerevisiae* according to [11] or [12], wherein the high-expression level glucuronosyl transferase is UGT1A7, UGT1A6, or UGT1A10.
[14]
The *Saccharomyces cerevisiae* according to any one of [1] to [13], used to produce a glucuronide of the substance being glucuronided.
[15]
A method for producing a glucuronide, comprising culturing the transformed *Saccharomyces cerevisiae* according to any one of [1] to [13] in the presence of glucose and a substance being glucuronided to cause a glucuronide of the substance being glucuronided to be produced.
[16]
The producing method according to [15], wherein the substance being glucuronided is at least one member selected from the group consisting of pharmaceuticals containing alcohol hydroxyl groups, candidate substances for such pharmaceuticals, polyphenol compounds comprising multiple phenol hydroxyl groups, non-steroidal anti-inflammatory drugs containing carboxylic acids, candidate substances for such drugs, and compounds comprising at least one primary to quaternary amine.
[17]
The producing method according to [15], wherein the substance being glucuronided is a substance producing a functional group (primarily a hydroxyl group) that undergoes glucuronidation when metabolized by P450.
[18]
The producing method according to [17] wherein the substance being glucuronided is at least one member selected from the group consisting of pharmaceuticals comprising methoxy groups or ethoxy groups, candidate substances for such pharmaceuticals, sesamin compounds having methylene dioxyphenyl groups, diazepine pharmaceuticals not comprising hydroxyl groups, and candidate substances for such pharmaceuticals.
[19]
A UDP-glucose dehydrogenase expression vector, comprising a UDP-glucose dehydrogenase gene inserted in an expressible manner in a *Saccharomyces cerevisiae* expression vector.
[20]
A UDP-glucuronosyl transferase expression vector, comprising a UDP-glucuronosyl transferase gene inserted in an expressible manner in a *Saccharomyces cerevisiae* expression vector.
[21]
A UDP-glucuronosyl transferase and UDP-glucose dehydrogenase expression vector, comprising a UDP-glucuronosyl transferase gene and a UDP-glucose dehydrogenase gene inserted in an expressible manner in a *Saccharomyces cerevisiae* expression vector.
[22]
The vector according to any one of [19] to [21], wherein the *Saccharomyces cerevisiae* expression vector is an autonomous replication vector or a chromosome integrative vector.
[23]
The vector according to any one of [15], [19], and [21] to [22], wherein the UDP-glucose dehydrogenase gene is a gene derived from an animal or a plant.
[24]
The vector according to any one of [19], and [21] to [22], wherein the UDP-glucose dehydrogenase gene is a gene derived from *Arabidopsis* or a gene derived from a rat.
[25]
The vector according to any one of [20] to [24], wherein the UDP-glucuronosyl transferase gene is a gene derived from a mammal.
[26]
The vector according to any one of [20] to [24], wherein the UDP-glucuronosyl transferase gene is a human-derived gene.

Effect of the Invention

The present invention permits the preparation of glucuronides using UDPGDH and UGT expression *Saccharomyces cerevisiae* cells. Based on the method for preparing glucuronides using genetically-altered *Saccharomyces cerevisiae* of the present invention, it is possible to prepare targeted metabolites extremely efficiently and economically relative to organic synthesis methods, in vitro enzymatic methods, and glucuronide preparation methods employing *Saccharomyces Pombe*. For example, as set forth in the Examples, a glucuronide of 7-hydroxycoumarin can be manufactured with a productivity of 200 mg per liter of reaction solution under optimal conditions employing *Saccharomyces cerevisiae* cells simultaneously expressing UDPGDH and UGT1A6.

Since there have been reports on genes of various UGT molecular species, the *Saccharomyces cerevisiae* cells expressing UDPGDH and UGT of the present invention can be used to prepare various UGT molecular species. As a result, the *Saccharomyces cerevisiae* cells expressing UDPGDH and UGT of the present invention can be applied to various pharmaceuticals and are highly practical.

Further, in the method of the present invention, *S. cerevisiae* is employed as a host yeast. Through a certain amount of effort, the following advantages have been achieved over the method described in Nonpatent Reference 7, which employs *S. Pombe* as host:

(1) With *S. Pombe*, the activity of UGT1A6 is extremely low, which is presumed to result in the low level of expression. However, with *S. cerevisiae*, the level of expression is high and activity is extremely high (FIG. 5; 100% conversion is achieved). Compared to the data for *S. Pombe* employing 4-methylunbelliferone as substrate, production capacity that was several ten-fold higher was actually exhibited in multiple molecular species (see Table 6).

(2) One type of ABC transporter present in *S. cerevisiae* is presumed to relate to secretion outside the cell body (FIG. 6). That is an unanticipated result, and is thought to be a phenomenon unique to *S. cerevisiae* that is not found in *S. Pombe*.

(3) In *S. Pombe*, UGT1A3, 1A4, and 2B7 are not well expressed. However, in *S. cerevisiae*, high expression of these compounds is achieved. High expression of 1A4 was successfully achieved by changing the signal sequence.

The main drawbacks of a UGT expression system employing *S. Pombe* as host in this manner are thought to be a low level of expression and differences in expression levels due to differences in molecular species.

By contrast, in the present invention, *S. cerevisiae* was employed as host and the N-terminal signal sequence was changed as needed. Thus, high expression of all UGT molecular species was successfully achieved and the main drawbacks of the *S. Pombe* expression system were successfully elucidated. Simultaneous expression with animal or plant-derived UDPGDH was successfully achieved, and highly efficient extracellular secretion and production of glucuronide were achieved with cells.

MODES OF CARRYING OUT THE INVENTION

[Transformed *S. cerevisiae*]

Figure 1:
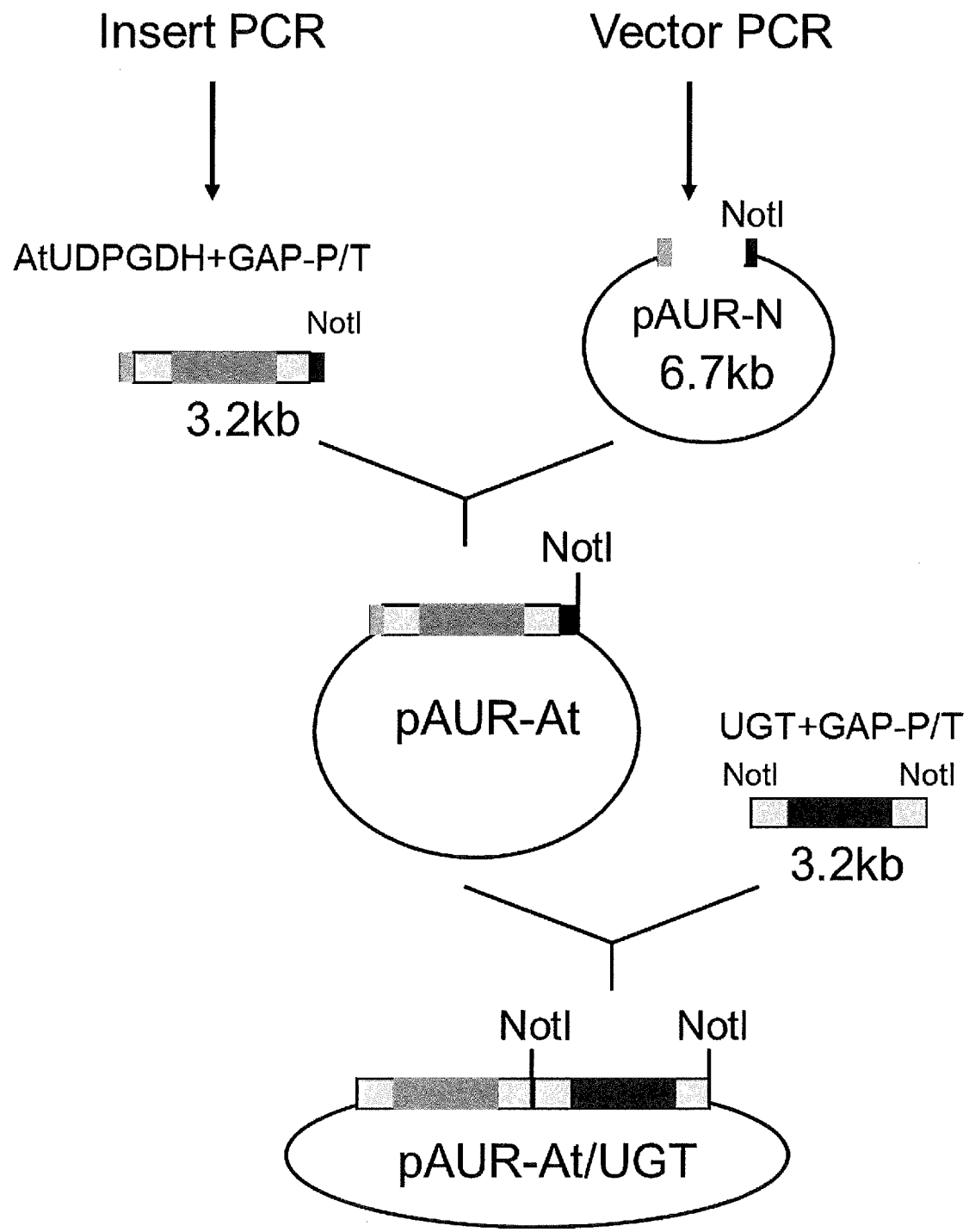
FIG. 1 shows the construction scheme of an autonomous replication yeast expression vector comprising both a UDP-glucuronosyl transferase gene and a UDP-glucose dehydrogenase gene.

The present invention relates to transformed *S. cerevisiae*. More specifically, the present invention relates to *S. cerevisiae* that is transformed by inserting in an expressible manner a gene coding for UDP-glucuronosyl transferase and a gene coding for UDP-glucose dehydrogenase. The transformed *S. cerevisiae* of the present invention can be *S. cerevisiae* that has been transformed by introducing in an expressible manner a gene coding for cytochrome P450 in addition to *S. cerevisiae* that has been transformed by inserting in an expressible manner a gene coding for UDP-glucuronosyl transferase and a gene coding for UDP-glucose dehydrogenase. The gene coding for UDP-glucose dehydrogenase, the gene coding for UDP-glucuronosyl transferase, and the gene coding for cytochrome P450 can be combined into an *S. cerevisiae* expression vector which is then inserted into *S. cerevisiae* to transform it. Alternatively, these genes can be inserted in an expressible manner into the chromosomes of the *S. cerevisiae* that is to be transformed by, for example, a known technique such as homologous recombination.

Examples of *S. cerevisiae* transformed by incorporating these genes into an *S. cerevisiae* expression vector and inserting it into *S. cerevisiae* are *S. cerevisiae* transformants selected from (A) to (G) below:

(A) *Saccharomyces cerevisiae* that has been transformed with a UDP-glucose dehydrogenase expression vector and a UDP-glucuronosyl transferase expression vector;

(B) *Saccharomyces cerevisiae* that has been transformed with a UDP-glucuronosyl transferase and UDP-glucose dehydrogenase expression vector;

(C) *Saccharomyces cerevisiae* that has been transformed with a UDP-glucose dehydrogenase expression vector, a UDP-glucuronosyl transferase expression vector, and a cytochrome P450 gene expression vector;

(D) *Saccharomyces cerevisiae* that has been transformed with a UDP-glucuronosyl transferase and UDP-glucose dehydrogenase expression vector, and a cytochrome P450 gene expression vector;

(E) *Saccharomyces cerevisiae* that has been transformed with a UDP-glucuronosyl transferase expression vector and a UDP-glucose dehydrogenase and cytochrome P450 gene expression vector;

(F) *Saccharomyces cerevisiae* that has been transformed with a UDP-glucuronosyl transferase and cytochrome P450 gene expression vector and a UDP-glucose dehydrogenase expression vector; and (G) *Saccharomyces cerevisiae* that has been transformed with a UDP-glucose dehydrogenase, UDP-glucuronosyl transferase, and cytochrome P450 gene expression vector.

For example, the above UDP-glucose dehydrogenase expression vector is comprised of a UDP-glucose dehydrogenase gene inserted in an expressible manner into a *S. cerevisiae* expression vector. The UDP-glucuronosyl transferase expression vector is comprised of a UDP-glucuronosyl transferase gene inserted in an expressible manner into a *S. cerevisiae* expression vector. The UDP-glucuronosyl transferase and UDP-glucose dehydrogenase expression vector is comprised of a UDP-glucuronosyl transferase gene and a UDP-glucose dehydrogenase gene inserted in an expressible manner into a *S. cerevisiae* expression vector. The various vectors will be described below.

[The Expression Vectors of Enzymes and the Like]

In the present invention, (1) a UDP-glucose dehydrogenase expression vector, (2) a UDP-glucuronosyl transferase expression vector, (3) a UDP-glucuronosyl transferase and UDP-glucose dehydrogenase expression vector, (4) a cytochrome P450 gene expression vector, (5) a UDP-glucuronosyl transferase and cytochrome P450 gene expression vector, (6) a UDP-glucose dehydrogenase and cytochrome P450 gene expression vector, and (7) a UDP-glucuronosyl transferase, UDP-glucose dehydrogenase, and cytochrome P450 gene expression vector are employed. When multiple genes are present in a single vector, the gene arrangement (order) is not limited. Each of (1), (2), and (4) will be sequentially described below. It is possible to suitably provide vectors (3), (5), (6), and (7), each of which comprises multiple genes in a single vector, based on the description of (1), (2), and (4).

<The UDP-Glucose Dehydrogenase Expression Vector>

The UDP-glucose dehydrogenase expression vector is comprised of a UDP-glucose dehydrogenase (UDPGDH) gene inserted into a yeast expression vector.

The expression vector into which the enzyme gene is inserted can be an autonomous replication vector that causes the *S. cerevisiae* host to replicate, retain, and express the enzyme gene, or a chromosome integrative plasmid vector that is integrated into a chromosome of *S. cerevisiae*. Any autonomous replication vector or chromosome integrative plasmid vector is retained by the host *S. cerevisiae* and functions can be used without limitation. Examples of autonomous replication vectors are the pGYR employed in the Examples, and yeast-derived plasmids YEp352GAP, YEp51, pSH19, and the like. An example of a chromosome integrative plasmid vector is the pAUR employed in the Examples.

The enzyme gene and, as needed, a signal sequence gene can be spliced downstream from a promoter in a vector suited to the above expression to obtain an expression vector. Examples of the promoter are EN01 promoter, GAL10 promoter, GAPDH promoter, and ADH promoter.

The UDP-glucose dehydrogenase gene can be derived from either an animal or a plant. The animal or plant-derived UDP-glucose dehydrogenase gene can be suitably selected from among known genes (such as the human gene: AF061016.1 and the mouse gene: AF061017.1). In the Examples, an *Arabidopsis*-derived gene and a rat-derived gene are employed. However, any UDP-glucose dehydrogenase gene can be introduced. The *S. cerevisiae* that has been transformed with the *S. cerevisiae* expression vector will have UDP-glucose dehydrogenase activity. Accordingly, regardless of its derivation, any known UDP-glucose dehydrogenase gene can be employed. The *Arabidopsis*-derived gene is available from a commercial cDNA library in the form of PCR ready First Strand cDNA (BIOCHAIN™). The rat-derived gene is available from a rat liver cDNA library in the form of PCR ready First Strand cDNA (BIOCHAIN™). In addition to these, UDP-glucose dehydrogenase genes can be suitably obtained from commercial cDNA libraries.

<The UDP-Glucuronosyl Transferase Expression Vector>

The UDP-glucuronosyl transferase expression vector is comprised of a UDP-glucuronosyl transferase (UGT) gene that is inserted into a *S. cerevisiae* expression vector. The same *S. cerevisiae* expression vector as that described for the UDP-glucose dehydrogenase expression vector can be employed.

The UDP-glucuronosyl transferase gene can be suitably selected from known genes. The UDP-glucuronosyl transferase gene can be derived from a mammal. Specifically, it can be a human-derived gene. UDP-glucuronosyl transferase (UGT) is an endoplasmic reticulum membrane protein comprised of about 530 amino acid residues. Multiple molecular species are present in the liver and small intestine. These molecular species are characterized in that the half on the amino terminal side (about 290 amino acid residues) comprises a domain recognizing a glucuronided substrate. The half on the carboxyl terminal side (about 240 amino acid residues), which exhibits high homology between molecular species, functions as the domain to which UDP-glucuronic acid binds and is the common substrate (Nonpatent References 3, 4, 10).

Many molecular species of the UDP-glucuronosyl transferase gene have been cloned in the research thus far and its base sequence has been determined (Nonpatent Reference 3). These known genes are suitably employed in the present invention. Examples of representative glucuronosyl transferases are human and pig-derived enzymes. The genetic sequences of these transferases and the genetic sequences of their signal sequences have, in the case of the human-derived enzyme, been recorded in GenBank, and in the case of the pig-derived enzyme, been recorded in PEDE (Database of full-length cDNA clones and ESTs in pigs) (http://pede.dna.affrc.go.jp). The sequence information is readily available. Typical examples of the UGT gene are given below.

TABLE 1

| human UGT1A | |
| --- | --- |
| UGT | Genbank Acc. No. |
| UGT1A1 | M57899 |
| UGT1A3 | M84127 |
| UGT1A4 | M57951 |
| UGT1A6 | M39570 |
| UGT1A7 | U89507 |
| UGT1A8 | U42604 |
| UGT1A9 | AF056188 |
| UGT1A10 | U89508 |
| UGT2B7 | J05428 |
| UGT2B10 | NM 001075 |
| UGT2B15 | U08854 |
| porcineUGT | |
| UGT | Clone name |
| Porcine UGT | OVRM1_0121_C02 |

Some expression systems of glucuronosyl transferase employing *S. cerevisiae* afford low expression levels depending on the molecular species. For molecular species with low expression levels in *S. cerevisiae*, for example, by raising the expression level of the UGT1A1 gene, the scope of pharmaceutical glucuronide metabolites that can be prepared is expanded and the practical value of glucuronide preparation methods based on *S. cerevisiae* expressed glucuronosyl transferase is increased substantially. In the present invention, in an expression system of glucuronosyl transferase employing *S. cerevisiae*, for molecular species with low expression levels in *S. cerevisiae*, the signal sequence gene is desirably replaced with the signal sequence gene of a high-expression glucuronosyl transferase.

A molecular species of the glucuronosyl transferase gene that affords a low expression level can be, for example, a low-expression level glucuronosyl transferase gene with an expression level of 50% or less than that of UGT1A7. The low-expression level glucuronosyl transferase can be UGT1A1, UGT1A4, UGT1A8, or UGT1A9, for example. However, no limitation thereto is intended. Further, the signal sequence gene of the low-expression level glucuronosyl transferase gene can be replaced with, for example, the signal sequence gene of a high-expression glucuronosyl transferase with an expression level of 80% or more of that of UGT1A7. Examples of high-expression glucuronosyl transferases are UGT1A7, UGT1A6, and UGT1A10. However, no limitation thereto is intended. Replacement with such a signal sequence strengthens the expression level of the glucuronosyl transferase by the *S. cerevisiae* transformant relative to that of a transformant in which the signal sequence gene has not been replaced.

The low-expression level glucuronosyl transferase gene can be (A) a gene coding for any one of amino acid sequences (a) to (c) indicated below; (B) a gene coding for an amino acid sequence comprising any one of the amino acid sequences (a) to (c) in which 1 to 5 amino acids have been substituted or deleted; or (C) a gene coding for an amino acid sequence comprising any one of amino acid sequences (a) to (c) to which 1 to 5 amino acids have been added. However, when the gene coding for the amino acid sequence with substitutions or deletions of (B) or the amino acid sequence with additions of (C) is employed as a signal sequence gene, the expression level of glucuronosyl transferase is 80% or more that of the wild strain.

```
(a)
                                    (SEQ. ID NO. 1)
MARAGWTGLLPLYVCLLLTCGFAKAG, (b)
                                    (SEQ. ID NO. 2)
MACLLRSFQRISAGVFFLALWGMVVG, (c)
                                    (SEQ. ID NO. 3)
MAPRRVDQPRSFMCVSTADLWLCEAG.
```

When the signal sequence gene of a low-expression level glucuronosyl transferase gene is replaced with (B) a gene coding for an amino acid sequence comprising any one of amino acid sequences (a) to (c) in which 1 to 5 amino acids have been substituted or deleted, and this gene is employed as the signal sequence gene of a glucuronosyl transferase gene, the gene is to have a glucuronosyl transferase expression level of 80% or more that of UGT1A7. When a gene coding for an amino acid sequence comprising the amino acid sequence of (a) in which 1 to 5 amino acids have been substituted or deleted is employed as a signal sequence gene, the UGT1A7 expression level of the gene is to be 80% or greater, desirably 90% or greater, and preferably, 100% that of UGT1A7 of the wild strain. When a gene coding for an amino acid sequence comprising the amino acid sequence of (b) in which 1 to 5 amino acids have been substituted or deleted is employed as a signal sequence gene, the UGT1A6 expression level of the gene is to be 80% or greater, desirably 90% or greater, and preferably, 100% that of UGT1A6 of the wild strain. When a gene coding for an amino acid sequence comprising the amino acid sequence of (c) in which 1 to 5 amino acids have been substituted or deleted is employed as a signal sequence gene, the UGT1A6 expression level of the gene is to be 80% or greater, desirably 90% or greater, and preferably, 100% that of UGT1A10 of the wild strain.

Further, when the signal sequence gene of a low-expression level glucuronosyl transferase gene is replaced with (C) a gene coding for an amino acid sequence comprising any one of amino acid sequences (a) to (c) to which 1 to 5 amino acids have been added, and this gene is employed as the signal sequence gene of a glucuronosyl transferase gene, the gene is to have a glucuronosyl transferase expression level of 80% or more that of UGT1A7. When a gene coding for an amino acid sequence comprising the amino acid sequence of (a) in which 1 to 5 amino acids have been added is employed as a signal sequence gene, the UGT1A7 expression level of the gene is to be 80% or greater, desirably 90% or greater, and preferably, 100% that of UGT1A7 of the wild strain. When a gene coding for an amino acid sequence comprising the amino acid sequence of (b) in which 1 to 5 amino acids have been added is employed as a signal sequence gene, the UGT1A6 expression level of the gene is to be 80% or greater, desirably 90% or greater, and preferably, 100% that of UGT1A6 of the wild strain. When a gene coding for an amino acid sequence comprising the amino acid sequence of (c) in which 1 to 5 amino acids have been added is employed as a signal sequence gene, the UGT1A6 expression level of the gene is to be 80% or greater, desirably 90% or greater, and preferably, 100% that of UGT1A10 of the wild strain.

The expression level of glucuronosyl transferase can be compared to that of the wild strain by, for example, analyzing by the Western blotting method or the like the expression of glucuronosyl transferase in the microsome fraction using a common sequence-recognizing peptide antibody of the human glucuronosyl transferase family (Nonpatent Reference 6).

Replacing the signal sequence gene of a low-expression level glucuronosyl transferase gene with a gene coding for the above amino acid sequence strengthens the level of expression of glucuronosyl transferase by the *S. cerevisiae* transformant relative to a transformant in which the signal sequence gene has not been replaced.

<The UDP-Glucuronosyl Transferase and UDP-Glucose Dehydrogenase Expression Vector>

The UDP-glucuronosyl transferase and UDP-glucose dehydrogenase expression vector is comprised of both a UDP-glucuronosyl transferase gene and a UDP-glucose dehydrogenase gene inserted into a single *S. cerevisiae* expression vector. The *S. cerevisiae* transformed with the vector will simultaneously exhibit UDP-glucuronosyl transferase and UDP-glucose dehydrogenase activity. The same *S. cerevisiae* expression vector as that described above for the UDP-glucuronosyl dehydrogenase expression vector can be employed. The same UDP-glucuronosyl transferase gene and UDP-glucose dehydrogenase gene as those set forth above can be employed.

The order in which the UDP-glucuronosyl transferase gene and the UDP-glucose dehydrogenase gene are inserted into the vector is not specifically limited. The expression of the individual enzyme genes is not impeded by one or the other being positioned upstream.

<The Cytochrome P450 Gene Expression Vector>

The cytochrome P450 gene expression vector is described in Nonpatent Reference 11 and can be prepared based on the description set forth therein. The same *S. cerevisiae* expression vector as that described for the UDP-glucose dehydrogenase expression vector above can be employed.

pGYR, which has a proven track record in the expression of cytochrome P450, an endoplasmic reticulum membrane enzyme, was employed as the cytochrome P450 gene expression vector. There are promoter and terminator regions derived from the glyceroaldehyde-3-phosphate dehydrogenase gene of *Zygosaccharomyces rouxii* in the expression-regulating region, permitting regular protein expression. Incorporating a *S. cerevisiae*-derived P450 reductase gene promotes a monooxygenase reaction based on P450 in the yeast by increasing the supply of electrons from NADPH.

<Preparation of the Expression Vector>

The methods of functionally splicing enzyme genes and, as needed, a cytochrome P450 gene, and introducing them into a suitable vector are known to persons having ordinary skill in the art. Examples are the methods described in *Molecular Cloning* (1989) (Cold Spring Harbor Lab.). The position of insertion into the recombinant vector can be any region that is not involved in replication of the recombinant vector. Normally, multicloning sites within the vector are employed.

[The Transformant]

The transformant of the present invention is comprised of *S. cerevisiae* that has been transformed with one or more of the vectors of the present invention set forth above. *Saccharomyces cerevisiae* is employed as host. There is no specific limitation other than that the strain belongs to *Saccharomyces cerevisiae*. For example *Saccharomyces cerevisiae* strain AH22, strain NA87-11A, and strain SHY3 can be employed.

*S. cerevisiae* strain AH22 is a respiration-deficient strain from which mitochondrial DNA has been deleted. It is known to be the optimal host for the expression of cytochrome P450 bound to an endoplasmic reticulum membrane. (Reference: T. Sakaki, M. Akiyoshi-Shibata, Y. Yabusaki, H. Ohkawa, Organella targeted expression of rat liver cytochrome P450c27 in yeast: genetically engineered alteration of mitochondrial P450 into a microsomal form creates a novel functional electron transport chain, *J. Biol. Chem.* 267 16497-16502.(1992).) Since strain AH22 lacks mitochondrial DNA, it does not form functional mitochondria. Instead, it develops endoplasmic reticulum membranes, increasing the sites where P450 and UGT are present. It is thus thought to be advantageous to the expression of these proteins. UDP-glucuronosyl transferase (UGT) is a protein that binds to endoplasmic reticulum membranes in the same manner as P450. Thus, strain AH22 is thought to be a suitable host for the expression of UGT. In the Examples, strain AH22 is employed as host. For reasons such as these, in a simultaneous cytochrome P450 and UGT expression system, strain AH22 is thought to be a desirable host. However, the present invention is not limited to cases where strain AH22 is used as host.

Examples of the transformant of the present invention are:

(A) *Saccharomyces cerevisiae* that has been transformed with a UDP-glucose dehydrogenase expression vector and a UDP-glucuronosyl transferase expression vector;

(B) *Saccharomyces cerevisiae* that has been transformed with a UDP-glucuronosyl transferase and UDP-glucose dehydrogenase expression vector;

(C) *Saccharomyces cerevisiae* that has been transformed with a UDP-glucose dehydrogenase expression vector, a UDP-glucuronosyl transferase expression vector, and a cytochrome P450 gene expression vector;

(D) *Saccharomyces cerevisiae* that has been transformed with a UDP-glucuronosyl transferase and UDP-glucose dehydrogenase expression vector, and a cytochrome P450 gene expression vector;

(E) *Saccharomyces cerevisiae* that has been transformed with a UDP-glucuronosyl transferase expression vector and a UDP-glucose dehydrogenase and cytochrome P450 gene expression vector;

(F) *Saccharomyces cerevisiae* that has been transformed with a UDP-glucuronosyl transferase and cytochrome P450 gene expression vector and a UDP-glucose dehydrogenase expression vector; and (G) *Saccharomyces cerevisiae* that has been transformed with a UDP-glucose dehydrogenase, UDP-glucuronosyl transferase, and cytochrome P450 gene expression vector.

The method of preparing the transformant is not specifically limited. Examples of methods of introducing a recombinant vector into a yeast host are: the electroporation method, the spheroplast method, and the lithium acetate method.

The transformant that has been prepared is cultured and grown by suitable usual methods, after which it can be used in the method for producing glucuronide, set forth further below. Although varying with the types of genes incorporated and the type of host, cells of the transformant that has been grown that are in the exponential growth phase will generally be suitable for use. There are also cases in which it is desirable to use cells prior to the exponential growth phase and cells subsequent to the exponential growth phase.

[The Method for Producing a Glucuronide]

The method for producing a glucuronide of the present invention comprises culturing the *Saccharomyces cerevisiae* transformant of the present invention in the presence of glucose and a substance being glucuronided to cause a glucuronide of the substance being glucuronided to be produced.

Figure 16:
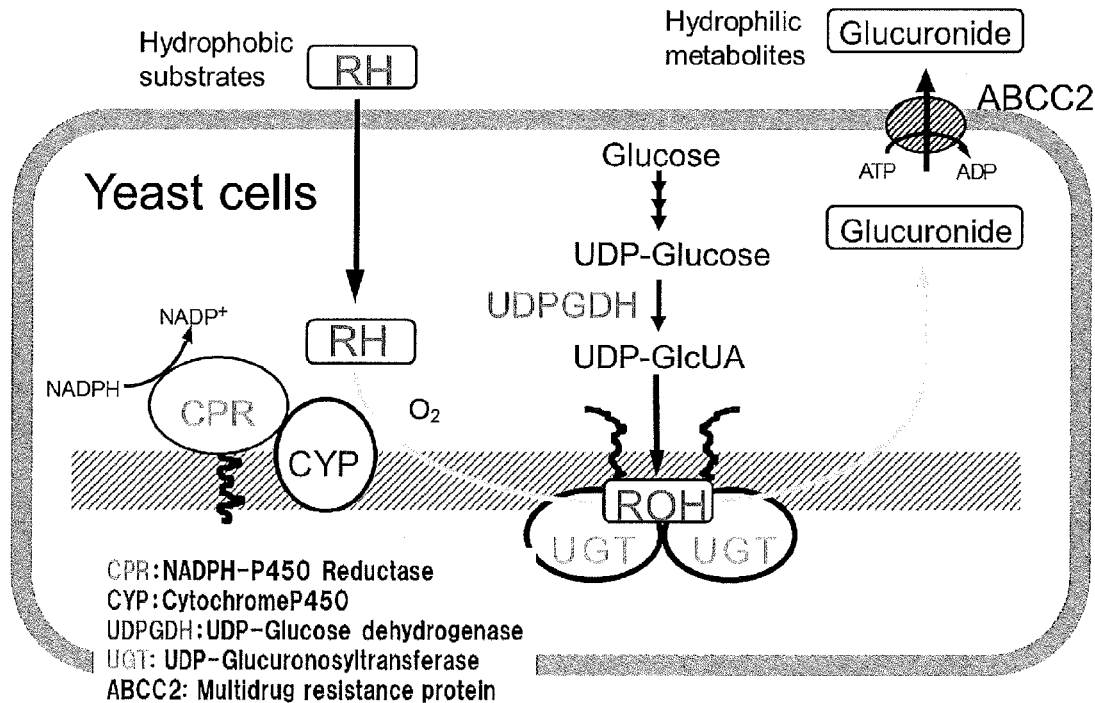
FIG. 16 shows a schematic descriptive diagram of the preparation of glucuronide employing recombinant yeast cells.

FIG. 16 shows a schematic descriptive diagram of the preparation of glucuronide employing the recombinant yeast cell (transformant) of the present invention.

Generally, foreign matter inside and outside the body (liposoluble compounds (hydrophobic substances)) (RH) undergoes a glucuronidation reaction and becomes a water-soluble glucuronide that is then eliminated to the exterior of the body. In particular, in glucuronides, the addition of glucuronic acid to a functional group such as a hydroxyl group, amino group, carboxyl group, or thiol group in a liposoluble compound converts it to a water-soluble polar metabolite. Elimination of the polar metabolite (glucuronide) to the exterior of the organism is promoted by multidrug resistance associated protein (ABCC2). Accordingly, the substance being glucuronided that is employed in the method for producing a glucuronide of the present invention can be a compound having a functional group such as the above-mentioned hydroxyl group, amino group, carboxyl group, or thiol group. These compounds can be pharmaceuticals or candidate substances for pharmaceuticals. When the substance being glucuronided comprises a functional group such as the above-mentioned hydroxyl group, amino group, carboxyl group, or thiol group, it is converted to a glucuronide by the glucuronosyl transfer reaction that is catalyzed by the UDP-glucuronosyl transferase (UGT, UDP-glucuronic acid transferase) within the cell with UDP-glucuronic acid (UDP-GlcUA) as a sugar donor.

Additionally, when no functional group such as a hydroxyl group, amino group, carboxyl group, or thiol group is present in the substance being glucuronided, the substance being glucuronided in the form of the liposoluble compound (hydrophilic substance) (RH, liposoluble substrate) inside or outside the organism is oxidized by cytochrome P450 (CYP) to form a hydroxide (ROH), and then converted to a glucuronide by the glucuronosyl transfer reaction that is catalyzed by the UDP-glucuronosyl transferase (UGT, UDP-glucuronic acid transferase) within the cell with UDP-glucuronic acid (UDP-GlcUA) as a sugar donor. This system, in which UDP-glucuronosyl transferase (UGT) is involved, is a foreign matter metabolizing system with the role of promoting the elimination of foreign matter to the exterior of the organism.

Additionally, UDP-glucuronic acid (UDP-GlcUA) is produced from glucose via UDP-glucose by the action of UDP-glucose dehydrogenase (UDPGDH). With the uptake of glucose in yeast, it is converted into UDP-glucose by the action of glucokinase, phosphomutase, and UTP glucose-1-phosphate uridyltransferase in glycolysis, the energy metabolism system. The sixth position of UDP-glucose is oxidized by the action of UDP-glucose dehydrogenase (UDPGDH) with NAD$^+$ as coenzyme, converting it to UDP-glucuronic acid (UDP-GlcUA).

As set forth above, in the method (Embodiment 1) employing a substance being glucuronided having a functional group such as a hydroxyl group, amino group, carboxyl group, or thiol group as a starting material, use of the transformant of (A), (B), or (E) above as the transformant of the present invention makes it possible to produce a glucuronide from the substance being glucuronided.

The substance being glucuronided having a functional group such as a hydroxyl group, amino group, carboxyl group, or thiol group is not specifically limited. Examples are pharmaceuticals containing alcohol hydroxyl groups, candidate substances for such pharmaceuticals, polyphenol compounds comprising multiple phenol hydroxyl groups, nonsteroidal anti-inflammatory drugs containing carboxylic acids, candidate substances for such drugs, and compounds comprising at least one primary to quaternary amine. Examples of these substances that are glucuronided are listed in Table 1 on pp. 100-102 of Nonpatent Reference 10. The entire contents of Table 1 on pp. 100-102 of Nonpatent Reference 10 are hereby incorporated by reference.

When the substance being glucuronided does not contain a functional group such as a hydroxyl group, amino group, carboxyl group, or thiol group, for example, a hydroxyl group can be incorporated by an organic synthesis method or selective hydroxylation can be conducted enzymatically employing cytochrome P450 to first incorporate a functional group into the substance being glucuronided, at which point the method of Embodiment 1 can be employed. Alternatively, when the substance being glucuronided does not contain a functional group such as a hydroxyl group, amino group, carboxyl group, or thiol group, the transformant of (C), (D), (E), (F), or (G) above into which the cytochrome P450 gene has been incorporated can be employed as the transformant of the present invention. This transformant can be cultured in the presence of glucose and the substance being glucuronided to produce a glucuronide of the substance being glucuronided (Embodiment 2). In the present invention, the metabolite obtained in the simultaneous P450 and UGT expression system is not specifically limited other than that it be produced by the glucuronidation of a functional group (primarily a hydroxyl group) by metabolism by P450. Examples are pharmaceuticals containing methoxy groups or ethoxy groups, candidate substances for such pharmaceuticals, sesamin compounds having methylene dioxyphenyl groups, diazepine pharmaceuticals not comprising hydroxyl groups, and candidate substances for such pharmaceuticals. In Embodiment 2, since a simultaneous expression strain containing cytochrome P450 is employed, a glucuronide can be prepared from a precursor (the substance being glucuronided) of the glucuronidation substrate. That is, a glucuronide can be prepared without converting the substance being glucuronided to a precursor (converting it to a hydroxide).

The substance being glucuronided that is employed in the producing method of the present invention is not specifically limited, as set forth above. That is because, in the present invention as set forth above, it is possible to suitably select the type of UDP-glucuronosyl transferase (UGT) gene that is contained in the transformant based on the type of substance being glucuronided that serves as the substrate for the UDP-glucuronosyl transferase (UGT). For example, in the examples given in the Examples, when preparing a glucuronide of 7-hydroxycoumarin (a phenol hydroxyl group), UGT1A6 is suitably employed as the UGT. When preparing a glucuronide (phenol hydroxyl group) of the 4' position and 3' position hydroxyl groups of quercetin, UGT1A1 or UGT1A8 is suitably employed as the UGT. When preparing a glucuronide (alcohol hydroxyl group) of the 7 position hydroxyl group of mycophenolic acid, UGT1A9 is suitably employed as the UGT.

The transformant of the present invention can be cultured by a culture method known to be suited to yeast in the presence of glucose and the substance being glucuronided. When the yeast host is strain AH22, it can synthesize all essential amino acids except L-histidine and L-leucine. Accordingly, these two amino acids are either added to the medium for culturing, or a vector having a gene for synthesizing either one of these amino acids can be employed as the expression vector to selectively culture a yeast host having the expression vector.

The culture conditions can be suitably set within conditions suited to the growth of yeast transformants. The culture medium employed to culture the transformant can be a natural medium or a synthetic medium, so long as it contains suitable proportions of a carbon source, nitrogen source, inorganic materials, and trace nutrients required by the bacterial strain employed, as needed. Alternatively, there are also sometimes cases where culturing can be conducted under conditions where at least some portion of the nutritional sources required for the yeast transformant to grow are lacking to achieve good production and accumulation of the glucuronide. There are also cases where these latter conditions are desirable based on the type of substance being glucuronided.

Any substance that can be utilized by a yeast transformant can be employed as a carbon source in the culture medium. Examples of substances that can be employed are: sugars such as glucose, maltose, fructose, mannose, trehalose, sucrose, mannitol, sorbitol, starch, dextrin, and molasses; organic acids such as citric acid and succinic acid; and fatty acids such as glycerol.

Various organic and inorganic nitrogen compounds can be incorporated as sources of nitrogen into the culture medium, and the medium can contain various inorganic salts. Examples of compounds that can be employed are: organic nitrogen sources such as corn steep liquor, soy meal, and various peptones; and inorganic nitrogen sources such as ammonium chloride, ammonium sulfate, urea, ammonium nitrate, sodium nitride, and ammonium phosphate. Amino acids such as glutamic acid and organic nitrogen sources such as urea can also serve as carbon sources. Nitrogen-containing natural materials such as peptones, polypeptones, bacto peptones, meat extracts, fish extracts, yeast extracts, corn steep liquor, soy flour, soy meal, dried yeast, casamino acids, and soluble vegetable proteins can also be employed as nitrogen sources.

Examples of inorganic materials that can be suitably employed in the culture medium are calcium salts, magnesium salts, potassium salts, sodium salts, phosphates, manganese salts, zinc salts, iron salts, copper salts, molybdenum salts, and cobalt salts. Specifically, dihydrogen potassium phosphate, hydrogen dipotassium phosphate, magnesium sulfate, ferrous sulfate, manganese sulfate, zinc sulfate, sodium chloride, potassium chloride, and calcium chloride can be employed. Further, as needed, trace quantity nutrients and vitamins such as amino acids, biotin, and thiamin can be suitably employed.

A liquid culturing method is good as the culturing method; any from among batch culturing, fed-batch culturing, continuous culturing, and perfusion culturing can be employed. Culturing methods employing aeration and agitation are industrially desirable. Culturing temperature and pH conditions that are optimal for the growth of the transformant employed can be selected. The culture period need only be greater than or equal to the period required for the microorganism to begin to grow, is desirably 8 to 120 hours, and is preferably the period at which the production of the genetic product of the recombinant protein gene peaks. For example, when culturing a transformant of S. cerevisiae, culturing is normally conducted with shaking or aeration and agitation under conditions selected from among a temperature of 20 to 40° C., desirably 25 to 35° C., a pH of 2 to 9, a desirable pH of 5 to 8, and a culturing period of from 0.5 to 7 days. The method of confirming growth of the yeast is not specifically limited. For example, the culture product can be collected and observed under a microscope, or the absorbance can be observed. The concentration of dissolved oxygen in the culture solution is not specifically limited. Normally, 0.5 to 20 ppm is desirable. To that end, it suffices to regulate the level of aeration, conduct stirring, or add oxygen to the airflow.

The quantity of transformant employed falls within a range of 0.5 to 5% (w/v, dry weight/volume of culture solution), for example. The quantities of glucose and substance being glucuronided that are added to the medium can be suitably determined taking into account the osmotic pressure in the medium and toxicity to the cells. By way of example, glucose suitably ranges from 4 to 20% (w/v) and the substance being glucuronided from 0.5 to 25 mM.

Glucuronide is accumulated in the culture product by culturing the transformant. Following culturing, the glucuronide is recovered from the culture solution of the yeast transformant. The glucuronide will often accumulate outside the transformant, but will sometimes accumulate within the transformant. The glucuronide that accumulates outside the transformant can be recovered by solvent extraction, for example. Recovery by solvent extraction can be conducted on the culture supernatant obtained once the transformant has been removed from the culture solution by the usual known methods. The transformant can also be re-utilized.

For glucuronide that accumulates within the transformant, for example, a transformant cell disruption product obtained by the method of dissolving the cell wall of the transformant with an organic solvent or an enzyme such as zymolyase, or obtained by a cell disruption method such as the ultrasonic disruption method, French press method, glass bead disruption method, or dyno-mill disruption method, and/or the culture product can be separated into transformant and culture supernatant by operations such as centrifugal separation and filtering. The glucuronide can then be recovered from the culture supernatant that has thus been obtained in the same manner as above.

The present invention will be described in detail below based on examples. However, the present invention is not limited to the examples.

EXAMPLE 1

1. Construction of Expression Vectors Containing UDP-Glucose Dehydrogenase Derived from *Arabidopsis thaliana* or Rat UDP-glucose dehydrogenase derived from *Arabidopsis thaliana* or rat was cloned from PCR amplification method using specific primers and cDNA library as templates. pGYR as multicopy plasmid (Ref.4) or pAUR101 as genome integrated plasmid (TAKARA™) were used in yeast expression system.

1-1. Cloning of UDP-Glucose Dehydrogenase Genes Derived from *Arabidopsis thaliana* or Rat.

1-1-1. Cloning of UDP-Glucose Dehydrogenase Genes Derived from *Arabidopsis thaliana*.

UDP-glucose dehydrogenase derived from *Arabidopsis thaliana* was cloned from PCR amplification method using specific primers and cDNA library as templates. PCR ready First Strand cDNA (BIOCHAIN™) was used as cDNA library.

KOD-plus-(TOYOBO™) was used as DNA polymerase. PCR amplification was performed in reaction condition and specific primers as described below;
Forward primer: SEQ. ID NO: 4
Revers primer: SEQ. ID NO: 5
PCR condition
Denature 94° C. 2 min
5 cycles 94° C. 15 sec, 37° C. 30 sec, 68° C. 1 min 45 sec
30 cycles 94° C. 15 sec, 55° C. 30 sec, 68° C. 1 min 45 sec
Extension 68° C. 10 min Analysis of PCR products using agarose gel electrophoresis resulted in the specific amplification of DNA fragment with 1.5 kb. After the PCR fragment of reaction mixture was separated, the purified fragment was cloned to pTA vector using TARGET CLONE™-plus-(TOYOBO™). The DNA sequence analysis of the resultant clone confirmed the gene product from GenBank Acc. No. AY056200 as showed in SEQ. ID no: 6.

To subclone into yeast expression vectors, several internal HindIII sites in the gene were changed without amino acid mutation. Introduction of mutations were performed using QUICK CHANGE™ (Agilent Technologies). The DNA sequence analysis of the resultant mutational clone confirmed the desirable mutational changes of the clone.

1-1-2. Cloning of UDP-Glucose Dehydrogenase Genes Derived from Rat.

UDP-glucose dehydrogenase derived from rat was cloned from PCR amplification method using specific primers and cDNA library as templates. PCR ready First Strand cDNA from liver (BIOCHAIN™) was used as cDNA library.

KOD-plus-(TOYOBO™) was used as DNA polymerase. PCR amplification was performed in reaction condition and specific primers as described below;
Forward primer: SEQ. ID NO: 7
Reverse primer: SEQ. ID NO: 8
PCR condition
Denature 94° C. 2 min
5 cycles 94° C. 15 sec, 37° C. 30 sec, 68° C. 1 min 45 sec
30 cycles 94° C. 15 sec, 55° C. 30 sec, 68° C. 1 min 45 sec
Extension 68° C. 10 min Analysis of PCR products using agarose gel electrophoresis resulted in the specific amplification of DNA fragment with 1.5 kb. After the PCR fragment of reaction mixture was separated, the purified fragment was cloned to pTA vector using TARGET CLONE™-plus-(TOYOBO™). The DNA sequence analysis of the resultant clone confirmed the gene product from GenBank Acc. No. 070199 as showed in SEQ. ID NO: 9.

To subclone into yeast expression vectors, several internal HindIII sites in the gene were changed without amino acid mutation. Introduction of mutations were performed using QUICK CHANGE™ (Agilent Technologies). The DNA sequence analysis of the resultant mutational clone confirmed the desirable mutational changes of the clone.

1-2. Construction of Expression Vector of UDP-Glucose Dehydrogenase.

1-2-1. Construction of Multicopy Yeast Expression Vectors.

After the digest of plasmids containing UDP-glucose dehydrogenase gene using Hind III at 37° C., 4 hrs as described in section 1-1-1 or 1-1-2, the resultant fragment of the genes (ca 1.5 kbp) were separated using agarose gel electrophoresis and WIZARD™ SV Gel and PCR Clean-Up System (PROMEGA™).

After the digest of pGYR as yeast expression vector using Hind III at 37° C., 4 hrs as described in section 1-1-1 or 1-1-2, the resultant fragment of the genes (ca 11 kbp) were separated using agarose gel electrophoresis and WIZARD™ SV Gel and PCR Clean-Up System (PROMEGA™).

After estimation of DNA concentration of insert and vector using agarose gel electrophoresis, mixture of each gene at 3:1 to 10:1 molecules was ligated at 16° C., 1 hr using DNA Ligation Kit Ver. 2 (TAKARA™). After the ligation reaction, E. coli JM109 was transformed with the reaction mixture and spread on LB agarose plate with 50 µg/ml ampicillin. To select the transformed colonies, direct PCR amplification were performed as colonies. EX TAQ™ (TAKARA™) was used as DNA polymerase. YGAP-P primer (SEQ. ID NO: 10) and reverse primers (SEQ. ID NO: 5 or 8) were used. PCR amplification was performed in reaction condition and specific primers as described below;

PCR condition
Denature 98° C. 5 min
30 cycles 94° C. 30 sec, 50° C. 30 sec, 72° C. 2 min 30 sec
Extension 72° C. 4 min After analysis of colony PCR, several clones with the desirable PCR amplification (ca 3 kbp) were obtained from LB plate. The resultant clones were cultivated with 5 ml LB medium with 50 µg/ml ampicillin at 37° C., 200 rpm, and 16 hrs. Each plasmid was purified from the cultures using alkaline-SDS method. Digest of plasmids with Hind III confirmed the construction of the two kinds of yeast expression vectors (pGYR/At.UDPGDH and pGYR/ratUDPGDH)

1-2-2. The Construction of Genome-Integrated Yeast Expression Vector

After the digest of pGYR/At.UDPGDH using Not I at 37° C., 4 hrs as described in section 1-2-2, the resultant fragment of the At.UDPGDH with yeast expression promoter and terminator (ca 3 kbp) were separated using agarose gel electrophoresis and WIZARD™ SV Gel and PCR Clean-Up System (PROMEGA™).

To insert the Not I DNA fragment of the At.UDPGDH with yeast expression promoter and terminator (ca 3 kbp) in genome-integrated yeast expression vector pAUR101 (TAKARA™), Not I site (GCGGCCGC) was generated at multicloning site of pAUR101 using site directed mutagenesis. Introduction of mutations were performed using QUICK CHANGE™ (Agilent Technologies). The DNA sequence analysis of the resultant mutational clone confirmed the desirable mutational changes of the clone (pAUR-N). After the digest of pAUR-N as yeast expression vector using Not I at 37° C., 4 hrs, the resultant fragment of the genes (ca 7 kbp) were separated using agarose gel electrophoresis and WIZARD™ SV Gel and PCR Clean-Up System (PROMEGA™).

After estimation of DNA concentration of insert and vector using agarose gel electrophoresis, mixture of each gene at 3:1 to 10:1 molecules was ligated at 16° C., 1 hr using DNA Ligation Kit Ver. 2 (TAKARA™). After the ligation reaction, E. coli JM109 was transformed with the reaction mixture and spread on LB agarose plate with 50 µg/ml ampicillin. The resultant clones were cultivated with 5 ml LB medium with 50 µg/ml ampicillin at 37° C., 200 rpm, and 16 hrs. The plasmid was purified from the cultures using alkaline-SDS method. Digest of plasmids with Not I confirmed the construction of the yeast expression vectors (pAUR/At.UDPGDH).

1-2-3. Construction of Genome-Integrated Yeast Expression Vector Containing UDP-Glucose Dehydrogenase and UDP-Glucuronosyl Transferase.

The genome-integrated yeast expression vector containing At.UDP-glucose dehydrogenase and UDP-glucuronosyl transferase were constructed using pAUR-N described in 1-2-2 (FIG. 1). Not I insert of UDPGDH and promoter/terminator without Not I site at promoter half and pAUR-N with complementary sequence to the insert were ligated using IN-FUSION™ Advantage PCR cloning kit (TAKARA™) to construct genome-integrated yeast expression vector containing UDPGDH and UGT (pAUR-At.UDPGDH).

Prime STAR Max Premix (TAKARA™) was used as DNA polymerase. PCR amplification was performed in reaction condition and specific primers as described below;

PCR of insert DNA;
Template: pGYR/At.UDPGDH
Forward primer: SEQ. ID NO: 11
Reverse primer: SEQ. ID NO: 12
PCR condition
Denature 98° C. 10 sec
30 cycles 98° C. 10 sec, 55° C. 5 sec, 72° C. 16 sec
Extension 72° C. 10 min
PCR of vector DNA;
Template: pAUR-N NotI digest
Forward primer: SEQ. ID NO: 13
Reverse primer: SEQ. ID NO: 14
PCR condition
Denature 98° C. 10 sec
30 cycles 98° C. 10 sec, 55° C. 5 sec, 72° C. 33 sec
Extension 72° C. 10 min After the digest of pGYR/UGT using Not I at 37° C., the resultant fragment of the UGT with yeast expression promoter and terminator (ca 3.2 kbp) were separated using agarose gel electrophoresis and WIZARD™ SV Gel and PCR Clean-Up System (PROMEGA™).

After the digest of pAUR-At.UDPGDH using Not I at 37° C., 4 hrs, the resultant fragment with single cut of Not I site (ca 10 kbp) was separated using agarose gel electrophoresis and WIZARD™ SV Gel and PCR Clean-Up System (PROMEGA™).

After estimation of DNA concentration of insert and vector using agarose gel electrophoresis, mixture of each gene at 3:1 to 10:1 molecules was ligated at 16° C., 1 hr using DNA Ligation Kit Ver. 2 (TAKARA™). After the ligation reaction, E. coli JM109 was transformed with the reaction mixture and spread on LB agarose plate with 50 µg/ml ampicillin. The resultant clones were cultivated with 5 ml LB medium with 50 µg/ml ampicillin at 37° C., 200 rpm, and 16 hrs. The plasmid was purified from the cultures using alkaline-SDS method.

Digest of plasmids with Not I confirmed the construction of the yeast expression vector containing UDPGDH and UGT (pAUR-At.UDPGDH/UGT).

TABLE 2

Combination of yeast expression vector in co-expression system

| Transformants | pGYR vector | pAUR vector |
|---|---|---|
| 1 |  | At.UDPGDH UGT |
| 2 | UGT | At.UDPGDH |

TABLE 2-continued

Combination of yeast expression vector in co-expression system

| Transformants | pGYR vector | pAUR vector |
|---|---|---|
| 3 | At.UDPGDH | UGT |
| 4 | RatUDPGDH | UGT |
| 5 | RatCYP | At.UDPGDH UGT |

TABLE 3

List of DNA sequences

| SEQ. ID NO | |
|---|---|
| 4 | cccaagcttaaaaaatggtgaagatatgctgcatagga |
| 5 | cccaagctttcatgccacagcaggcatatccttgagcc |
| 6 | atggtgaagatttgctgcattggagctggatatgttggtggtccaaccatggctgtcattgctctaaa<br>gtgtccatctgttgaagtagctgttgttgatatctctgtgccaaggatcaatgcctggaacagtgatc<br>agttaccgatctatgagcctggtcttgatgatgtcgttaagcagtgccgtggaaagaatctcttcttca<br>gcaccgatgttgagaaacatgtgagagaggctgacattgtttttgtgtctgtcaacaccccctactaa<br>gacccgtggtcttggagctggcaaagctgcggatttgacttactgggagagcgctgctcgtatgat<br>tgccgatgtttcggtttccgacaagattgttgttgagaaatcaactgttcctgtcaaaaccgcagag<br>gcaattgagaagattcttacacacaacagcaaaggaatcaaattccagattctgtcaaaccctga<br>gttccttgctgaaggaaccgctattgaagacctttttcatgcctgaccgtgtcctcatcggtggtcgtg<br>aaacaactgaaggctttgcagccgtcaaagccttgaaagacatttatgcccaatgggtccctgaa<br>gagagaatcctcaccaccaatctatggtctgccgagcttttccaagcttgcagctaatgccttcctag<br>cccagagaatctcatcagtcaatgcaatgtccgctctctgtgaggcaactggcgccaatgtctcag<br>aggtctcttatgctgtgggcaaagactctcgtattggtcccaagttcttgaactctagtgttgggttcgg<br>aggatcttgtttccagaaagatattctcaacttagtctacatctgcgaatgcaacggcttacccgaa<br>gttgctgagtactggaaacaagtcatcaagatcaacgactaccagaaaacccgatttgttaaccg<br>cattgtctcttcaatgtttaacacagtctccaacaaaaagattgcggttctcggcttcgcttttcaagaa<br>agacactggagacactagagagactccagccattgatgtctgcaaaggtctgttaggtgacaag<br>gctcgtctcagcatctacgacccacaagtcactgaagagcagatccaaagagacttaaccatga<br>acaaattcgactgggaccacccacttcatctccagcccatgagcccccaccactgtgaagcaagt<br>ctcagtcgcttgggacgcatacactgcaaccaaagacgcccacggtatctgcattttaaccgagt<br>gggacgagttcaagaaacttgatttccagcggatctttgagaatatgcagaaaccggcttttgttttt<br>gacggtagaaacgtggtcgacgctgataaactcagggagattgggtttattgtttactccattggta<br>agccattggaccagtggctcaaggacatgcctgctcttgcctaa |
| 7 | cccaagcttaaaaaatggttgagatcaagaagatctgt |
| 8 | cccaagcttctagactttgggcttcttgttaggtggat |
| 9 | atggttgagatcaagaagatctgttgcattggtgcgggctacgtcggcggacccacatgcagtgt<br>cattgctcgcatgtgccctgaaatcagggtaacggttgtggatgtcaatgaggccaggatcaatg<br>catggaattctccaacgcttcctatttatgagcctggactaaaagaagtagtcgaatcctgtcgagg<br>gaaaaacctcttttttttctaccaatattgatgatgccatcagagaagccgatctagtgttatttctgtg<br>aacacaccaacaaaaacatatggaatgggaaaaggccgggcggcagatctgaagtatatcg<br>aagcttgtgctcgccgcattgtgcagaactcaaatgggtacaaaattgtgactgagaaaagcac<br>agtccctgtgcgggcagcggaaagcatccgccgcatatttgatgccaacacaaagcccaacttg<br>aatctacaggttctgtccaatcctgagttcttggcagagggaacagccatcaaggacctaaagaa<br>cccagacagagtcctgattggaggggatgagaccccagagggccagagagctgttcaggcac<br>tctgtgctgtgtacgagcactgggttcccaaggaaaagatcctcaccaccaacacttggtcctcag<br>agctttccaaactggcagccaatgcttttcttgcccagaggatcagcagcattaactccataagtgc<br>tctgtgtgaaagcacaggcgccgatgtggaagaggtggcaacggctatcgggatggaccaaa<br>gaattggaaataagtttctaaaagccagcgttggttttggtggggctgcttccaaaaagatgttct<br>gaatttggtttatctctgtgaggctctgaatctgcccgaagtagctcgttactggcagcaggtcatag<br>acatgaatgactaccaggaggaggtttgcatcacggatcatagacagcctgtttaatacagtg<br>actgataagaagatagctatcttgggtttgcgttcaaaaaggatactggtgataccagggagtcc<br>tccagtatctacattagcaaatacctgatggacgagggtgcgcacctccacatctacgaccccaa<br>agtacccagggagcagatagtggtggatctttctcatccaggcgtctcagcggatgaccaagtgt<br>ccagactggtgaccatttccaaggatccatatgaagcatgtgatggcgcccatgccctcgttatctg<br>cacagagtgggacatgtttaaggaactggattatgaacggattcataaaagaatgctgaagcca<br>gccttcatatttgatgccggcgtgtcctggatgggctccacaatgagctacagaccattggcttcc<br>agattgaaacaattggcaaaaaggtatcttccaagagaattccatacactcctggtgaaattcca<br>aagtttagtcttcaggatccacctaacaagaagcccaaagtctag |
| 10 | aatgacaccgtgtggtgatcttcaagg |
| 11 | gttgaagcttgcatggataagaatgcagaaagccc |

TABLE 3-continued

List of DNA sequences

| SEQ. ID NO | |
|---|---|
| 12 | acggccagtgaattcgcggccgcgatccgggcgtc |
| 13 | gaattcactggccgtcgttttacaacgtcgtgact |
| 14 | catgcaagcttcaacagaggaaagaataacgcaaa |

1-2-4. Construction of Expression Plasmid of Modified UDP-Glucuronosyl Transferase To enhance the expression level of UGT1A1 and 1A9 in this study, N-terminal sequences of the UGT were modified to replacement of the signal sequence of UGT1A7 with high level of expression.

Table 4 showed the DNA sequences of N-terminal signal peptide in human UGT. (SEQ. ID NO: 15-17). To make the replacement of N-terminal region of UGT1A1 and 1A9, PCR amplification was performed using pUC119 with UGT cDNA and specific primers with modified sequences (Table 5; SEQ. ID NO: 18-20).

[Table 4]

TABLE 4

Table 4 the DNA sequences of N-terminal signal peptide in human UGT

| SEQ. ID NO: | |
|---|---|
| 15 (UGT1A7) | atg gct cgt gca ggg tgg act ggc ctc ctt ccc cta tat gtg tgt cta ctg acc tgt ggc ttt gcc aag |
| 16 (UGT1A1) | atg gct gtg gag tcc agg ggc gca cgc cca ctt gtc ctg ggc ctg ctg ctg tgt gtg ctg ggc cca gtg gtg |
| 17 (UGT1A9) | atg gct tgc aca ggg tgg acc agc ccc ctt cct cta tgt gtg tgt ctg ctg ctg acc tgt ggc ttt gcc gag gca ggg |

[Table 5]

TABLE 5

Table 5 the DNA sequences of modified PCR with N-terminal signal peptide in human UGT

| SEQ. ID NO: | |
|---|---|
| 18 (1A7-1A1) | 5'-cccaagcttaaaaaaatggctcgtgcagggtggactggcctccttcccctatatgtgtgtctactgctgacctgtggctttgccaaggctgggaagatactgttg-3' |
| 19 (1A7-1A9) | 5'-cccaagcttaaaaaaatggctcgtgcagggtggactggcctccttcccctatatgtgtgtctactgctgacctgtggctttgccaaggcagggaagctactggta-3' |
| 20 (UGT commonly used) | 5'-cccaagcttgatatcttctcaatgggtcttggatttgtgggcttt-3' |

1-2-4-1. Construction of N-Terminal Modified UGT Genes

To make the replacement of N-terminal region of UGT1A1 and 1A9], PCR amplification were performed using pUC119 with UGT cDNA and specific primers with modified sequences. KOD-plus-(TOYOBO™) was used as DNA polymerase. PCR amplification was performed in reaction condition and specific primers as described below;
Primer
Forward primer: SEQ. ID NO: 15 or 16
Reverse primer: SEQ. ID NO: 20
PCR condition
Denature 94° C. 2 min
5 cycles 94° C. 15 sec, 37° C. 30 sec, 68° C. 1 min 45 sec
30 cycles 94° C. 15 sec, 55° C. 30 sec, 68° C. 1 min 45 sec
Extension 68° C. 4 min Analysis of PCR products using agarose gel electrophoresis resulted in the specific amplification of DNA fragment with 1.6 kb. After digest of the modified UGT fragment using Hind III at 37° C., 1 hrs, the resultant fragment of the genes were separated using agarose gel electrophoresis and WIZARD™ SV Gel and PCR Clean-Up System (PROMEGA™).

After the digest of pUC119 as subcloning vector using Hind III at 37° C., 4 hrs, the resultant fragment of the genes (ca 2.8 kbp) were separated using agarose gel electrophoresis and WIZARD™ SV Gel and PCR Clean-Up System (PROMEGA™).

After estimation of DNA concentration of insert and vector using agarose gel electrophoresis, mixture of each gene at 3:1 to 10:1 molecules was ligated at 16° C., 1 hr using DNA Ligation Kit Ver. 2 (TAKARA™). After the ligation reaction, E. coli JM109 was transformed with the reaction mixture and spread on LB agarose plate with 50 µg/ml ampicillin.

To select the transformed colonies, direct PCR amplification were performed as colonies. EX TAQ™ (TAKARA™) was used as DNA polymerase. M13-M4 as forward primer and M13-Rev as reverse primers (SEQ. ID NO: 5 or 8) were used. PCR amplification was performed in reaction condition and specific primers as described below;
PCR condition
Denature 98° C. 5 min
30 cycles 94° C. 30 sec, 50° C. 30 sec, 72° C. 2 min
Extension 72° C. 4 min After analysis of colony PCR, several clones with the desirable PCR amplification (ca 1.6 kbp) were obtained from LB plate To confirm the correct sequence of PCR products, these clones were sequenced. The resultant clones were cultivated with 5 ml LB medium with 50 µg/ml ampicillin at 37° C., 200 rpm, and 16 hrs. Each plasmid was purified from the cultures using WIZARD™ Plus SV Minipreps DNA Purification System (PROMEGA™). Cycle sequencing were performed using BIGDYE™ Terminator v3.1 Cycle Sequencing Kit (Applied Biosystems). Analysis of the DNA sequences confirmed the modification of N-terminal region of UGT1A1 or 1A7 with replacement of that of UGT1A7.

1-2-4-2. Construction of Yeast Expression Vector with N-Terminal Modified UGT Genes After the digest of pUC119/UGT as described in 1-2-4-1 using Hind III at 37° C., the resultant fragment of the UGT were separated using agarose gel electrophoresis and WIZARD™ SV Gel and PCR Clean-Up System (PROMEGA™).

After the digest of pGYR using Hind III at 37° C., 4 hrs, the resultant fragment with single cut of Hind III (ca 11 kbp) was separated using agarose gel electrophoresis and WIZARD™ SV Gel and PCR Clean-Up System (PROMEGA™).

After estimation of DNA concentration of insert and vector using agarose gel electrophoresis, mixture of each gene at 3:1 to 10:1 molecules was ligated at 16° C., 1 hr using DNA Ligation Kit Ver. 2 (TAKARA™). After the ligation reaction, E. coli JM109 was transformed with the reaction mixture and spread on LB agarose plate with 50 µg/ml ampicillin. To select the transformed colonies, direct PCR amplification were performed as colonies. EX TAQ™ (TAKARA™) was used as DNA polymerase. YGAP-P primer (SEQ. ID NO: 10) and reverse primers (SEQ. ID NO: 20) were used. PCR amplification was performed in reaction condition and specific primers as described below;

PCR condition
Denature 98° C. 5 min
30 cycles 94° C. 30 sec, 50° C. 30 sec, 72° C. 2 min
Extension 72° C. 4 min After analysis of colony PCR, several clones with the desirable PCR amplification (ca 3 kbp) were obtained from LB plate The resultant clones were cultivated with 5 ml LB medium with 50 µg/ml ampicillin at 37° C., 200 rpm, and 16 hrs. Each plasmid was purified from the cultures using alkaline-SDS method. Digest of plasmids with Hind III confirmed the construction of the two kinds of yeast expression vectors (pGYR/UGT1A1 and pGYRUGT1A9)

EXAMPLE 2

2. Construction of Budding Yeast Co-Expression System Containing UDP-Glucose Dehydrogenase and UDP-Glucuronosyl Transferase 2-1. Transformation of Budding Yeast Cells with Expression Plasmid For yeast expression, budding yeast cells (*Saccharomyces cerevisiae*) AH22 strain was used. AH22 strain is able to synthesize essential amino acids except for L-histidine and L-leucine. AH22 transformant with pGYR is able to grow in SD medium with L-histidine because of the ability of pGYR to synthesize L-leucine. Because genome-integrated vector pAUR has an aureobasdin A-resistant gene, AH22 transformant with pAUR is able to grow in YPD medium with aureobasdin A. Yeast strain AH22 is transformed with expression plasmids to make the transformant using lithium chloride method. Table 2 shows the combination of expression vectors for the co-expression system. A detailed protocol is shown in the section below.

<Materials>

YPD medium: 1% (w/v) yeast extracts, 2% (w/v) polypeptone, 2% (w/v) glucose SDplate: 2% (w/v) glucose, 0.67% (w/v) N-base w/o amino acid, 1.5% (w/v) agar, 20 µg/ml L-histidine, 0.2M LiCl: 10 ml (filter sterilized), 1M LiCl: 10 ml (filter sterilized) 70% (w/v) PEG 4000: 10 ml <Methods>

After overnight culture of *S. cerevisiae* AH22, pellet of yeast ($1.0 \times 10^7$ cells) was obtained by centrifugation with 13,000 rpm, 4 min. The resultant pellet was washed by solution of 0.2M LiCl. After centrifugation with 13,000 rpm, 4 min, supernatant was completely removed. The pellet was resuspended with 20 µl of 1M LiCl. Plasmid solution (0.5-1 µg DNA/10 µl) and 70% (w/v) PEG 4(30 µl) were added to yeast-LiCl solution and gently suspend with pipetting procedure. After incubation with 40° C., 30 min, sterilized water (140 µl) was added to transformation mixture. For single transformant of pGYR and pAUR, the transformants were spread on SD agar plate and YPD agar plate with 0.5 µg/ml Aureobasidin A, respectively. After 3-5 days-inoculation at 30° C., several colony of transformants with 3-5 mm diameters were obtained. For co-expression of pGYR and pAUR, the transformants were spread on SD agar plate and YPD agar plate with 0.5 µg/ml Aureobasidin A, respectively. After 3-5 days-inoculation at 30° C., several colony of transformants with 3-5 mm diameters were obtained.

2-2. Confirmation of Expression of UDP-Glucose Dehydrogenase and UDP-Glucuronosyl Transferase in Yeast Cells.

Functional expression of UDPGDH and UGT in yeast cell were confirmed using western blot analysis and enzymatic assay of UDPGDH activity.

After selected transformants were cultivated in selection medium at 30° C., 48 hrs, zymolyase-treated yeast cells were disrupted using sonication, and the resultant solution were centrifuged to prepare the post mitochondrial fraction containing cytosol. For assay of UDP-glucose dehydrogenase, the reaction mixture containing enzyme, 5 mM UDP-glucose, and 0.5 mM $NAD^+$, 50 mM Tris-HCl (pH8.6) was incubated at 37° C., 1 hr, and the supernatant was prepared by centrifugation. Produced UDP-glucuronic acid in enzyme reaction was isolated and detected by C18-column-HPLC system with isocratic 20 mM trietylamine-acetate (pH 7.0), flow rate; 1 ml/min, detection; 260 nm. The post mitochondrial fraction of yeast transformant with UDPGDH gene (pGYR/At.UDPGDH) showed the enzymatic activity of UDP-glucose dehydrogenase (FIG. 2).

Figure 2:
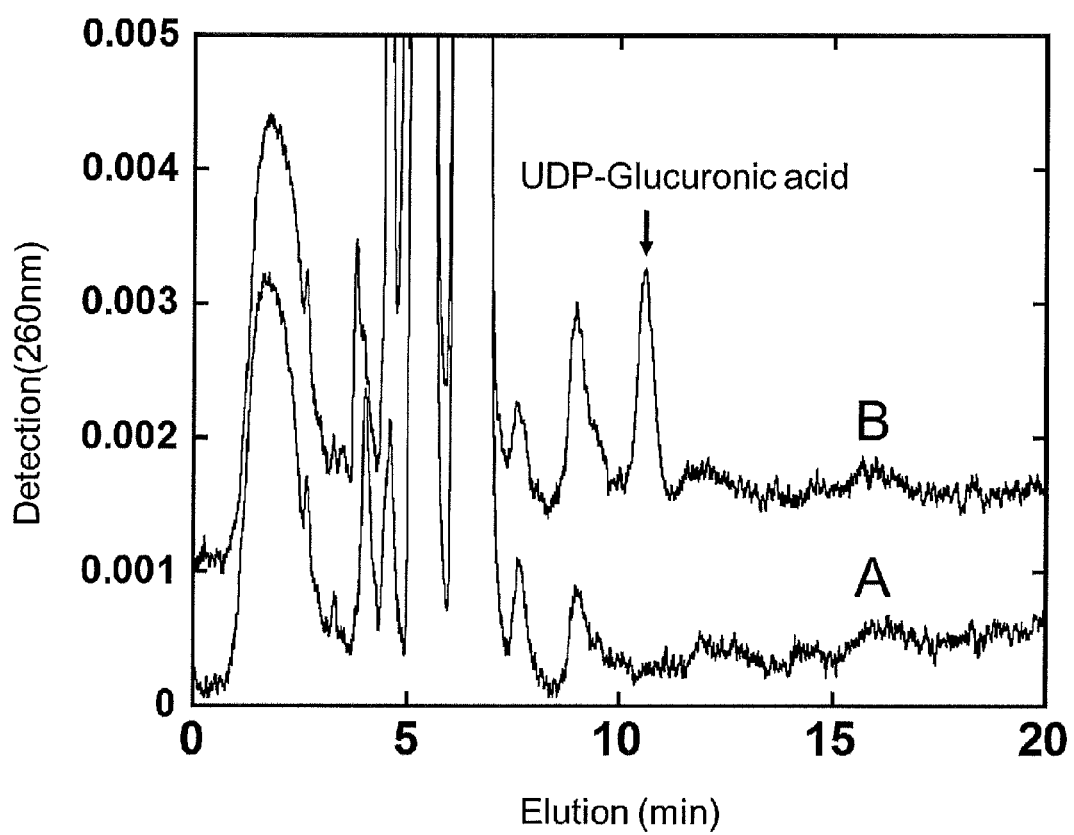
FIG. 2 shows the results of enzymatic activity measurement of UDP-glucose dehydrogenase expressed in yeast.

FIG. 2 indicated reverse phase HPLC elution pattern of production of UDP-glucuronic acid by UDPGDH in yeast. A:AH22:pAUR (control), B:AH22:pAUR/At.UDPGDH. The post mitochondrial fraction of yeast transformant with UDPGDH gene (pGYR/At.UDPGDH) showed the production of UDP-glucuronic acid with elution time around 11 min.

Figure 3:
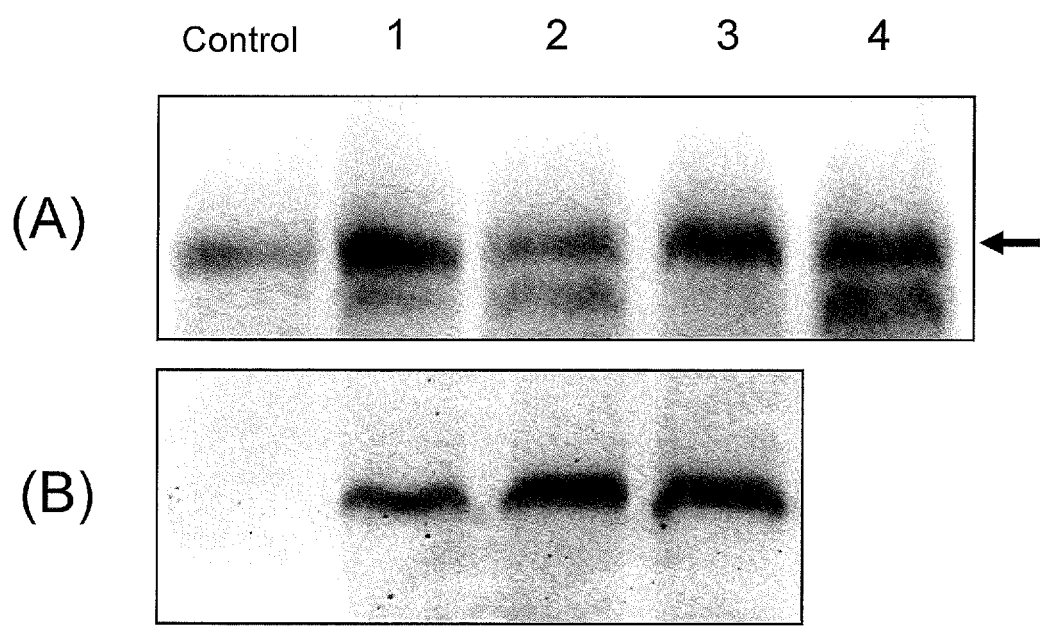
FIG. 3 shows the results, observed by the Western blotting method, of UDP-glucose dehydrogenase protein and UDP-glucuronosyl transferase gene expression in yeast.

Zymolyase-treated yeast cells were analyzed by western blot using antipeptide antibodies against commonly used C-terminal region of human UGT (Ref.5) or C-terminal region of At.UDPGDH (KPLDQWLKDMPALA) (FIG. 3). To confirm the expression of UDP-glucose dehydrogenase and UDP-glucuronosyl transferase in yeast cells, the post mitochondrial fraction of yeast transformants (No. 1-4 in Table 2) were analyzed by western blot. Panel (A): anti-UGT1A antibody, Panel (B): anti-At.UDPGDH antibody. Lane 1-3 in Panel (A) showed the expression of At.UDPGDH proteins but not control lane in Panel (B) (AH22: pGYR/UGT1A6). The expression of UDP-glucose dehydrogenase and UDP-glucuronosyl transferase in the post mitochondrial fraction of yeast transformants were confirmed by western blot.

2-3. Production of UDP-Glucuronic Acid Using Resting Yeast Cells

Production of UDP-glucuronic acid in yeast cells was confirmed by detection of endogenous UDP-glucuronic acid.

After selected transformants were cultivated in selection medium at 30° C., 48 hrs, 2.5-fold volume of chloroform: methanol (3:1, v/v) was added to culture medium containing yeast cells. Upper water phase of extracts were separated by centrifugation. Endogenous UDP-glucuronic acid in yeast cells was isolated and detected by WAKOPAK™ Navi C30-5 (3 mm×150 mm, Wako Chemical)-column-HPLC system with isocratic 20 mM trietylamine-acetate (pH 7.0), flow rate; 0.35 ml/min, detection; 260 nm.

Figure 4:
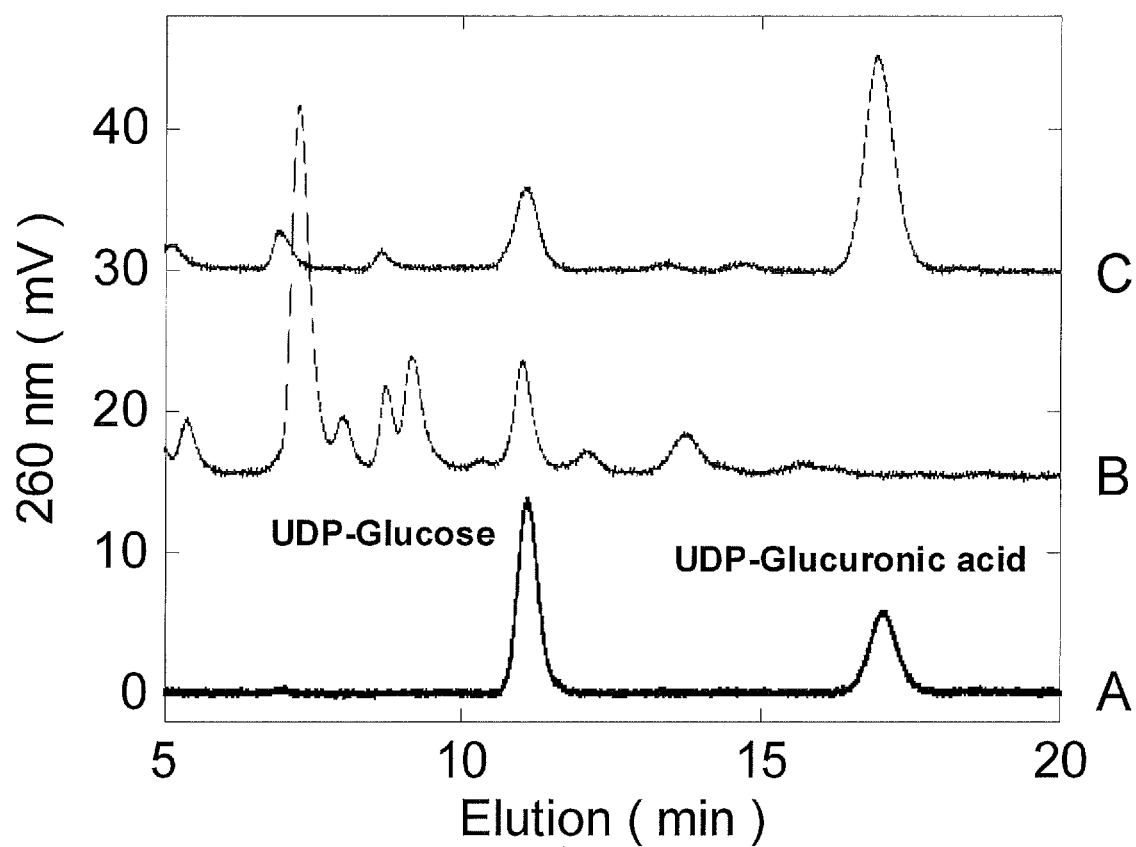
FIG. 4 shows the results of the production of UDP-glucuronic acid in yeast cells into which the UDP-glucose dehydrogenase gene has been introduced.

FIG. 4 indicated reverse phase HPLC elution pattern of endogenous UDP-glucuronic acid in yeast. Line A, B and C in FIG. 4 showed standard of UDP-glucuronic acid and UDP-glucose, control yeast (AH22: pGYR), and rat UDP-glucose dehydrogenase gene-transformed yeast, respectively. While only UDP-glucose was detected as sugar-nucleotide in line B, UDP glucuronic acid in addition to UDP-glucose was detected in line C. Based on the estimation of sugar nucleotide, concentration of endogenous UDP-glucuronic acid is about 4-5 mM in yeast cells.

Application 3

3. Production of Glucuronide Using Transformed Yeast Cells with UDPGDH and UGT 3-1. Production of 7-Hydroxycoumarine Glucuronide Using Resting Yeast Cells To confirm the production of 7-hydroxycoumarine glucuronide in the resting yeast cells containing UDPGDH and UGT, transformants were cultivated in selection medium at 30° C., 48 hrs, and the resultant yeast cells were suspended with appropriate buffer solution containing 0.1-1 mM 7-hydroxycoumarine and 1-8% (w/v) glucose. After incubation at 30° C., 24 hrs, 2-fold volume of chloroform:methanol (3:1, v/v) was added to reaction medium containing yeast cells. Centrifugation of extracts was separated to upper water and lower organic phase. Lower organic phase were evaporated and redissolved in 200 μl acetonitrile. Each phase was analyzed by UPLC system. Condition of analysis are described below; column: Cosmosil 2.5C18-MS-II (2.0 mm×100 mm, nacalai tesque), flow rate 0.5 ml/min, detection 320 nm, temperature 45° C. Condition of gradient elution: water-acetonitrile with 0.5% (v/v) trifluoroacetic acid, 10% (v/v) acetonitrile (4 min), 10-70% acetonitrile (6 min), 70-10% acetonitrile (2 min), 10% acetonitrile (4 min).

3-1-1. Production of Glucuronide Using Human UGT Co-Expression Systems

Production of glucuronide of 7-hydroxycoumarine in yeast cells with UDPGDH and UGT (AH22: pAUR/At.UDPGDH+pGYR/hUGT1A1, 1A6, 1A7, 1A8, 1A9) were confirmed by analysis of glucuronide formation.

Figure 5:
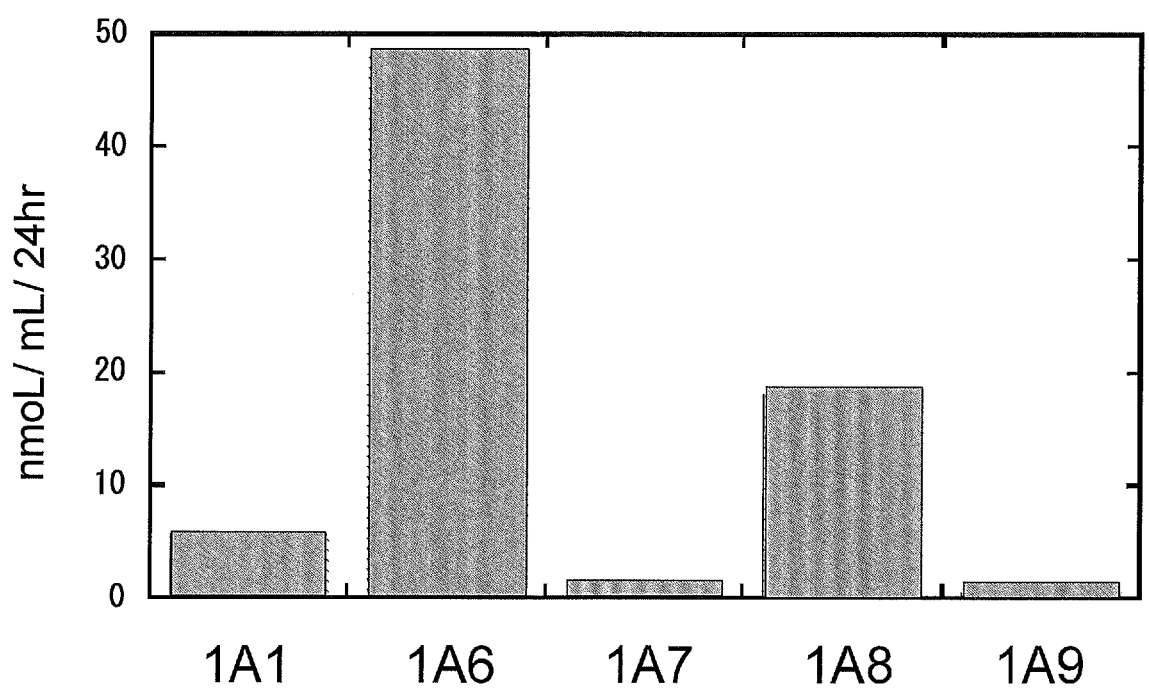
FIG. 5 shows the results of the production of glucuronide in yeast simultaneously expressing various human UDP-glucuronosyl transferases.

As showed in FIG. 5, production of glucuronide of 7-hydroxycoumarine were observed in co-expressed UGT isoforms (UGT1A1, 1A6, 1A7, 1A8, and 1A9) with UDPGDH. In co-expressed UDPGDH and UGT, UDPGDH is able to supply the UDP-glucuronic acid and UGT catalyzes the glucuronidation of exogenous substrates. As shown in FIG. 5, multiple utilization of UGT isoforms with different substrate- and region-specificity allows us to produce the variety of glucuronide in co-expression system.

3-1-2. Time Course of the Production of Glucuronide in UGT1A6 Co-Expression System Time course of conversion in the transformant with the highest activity of glucuronidation (AH22: pAUR/At.UDPGDH+pGYR/hUGT1A6) was examined (FIG. 6).

Figure 6:
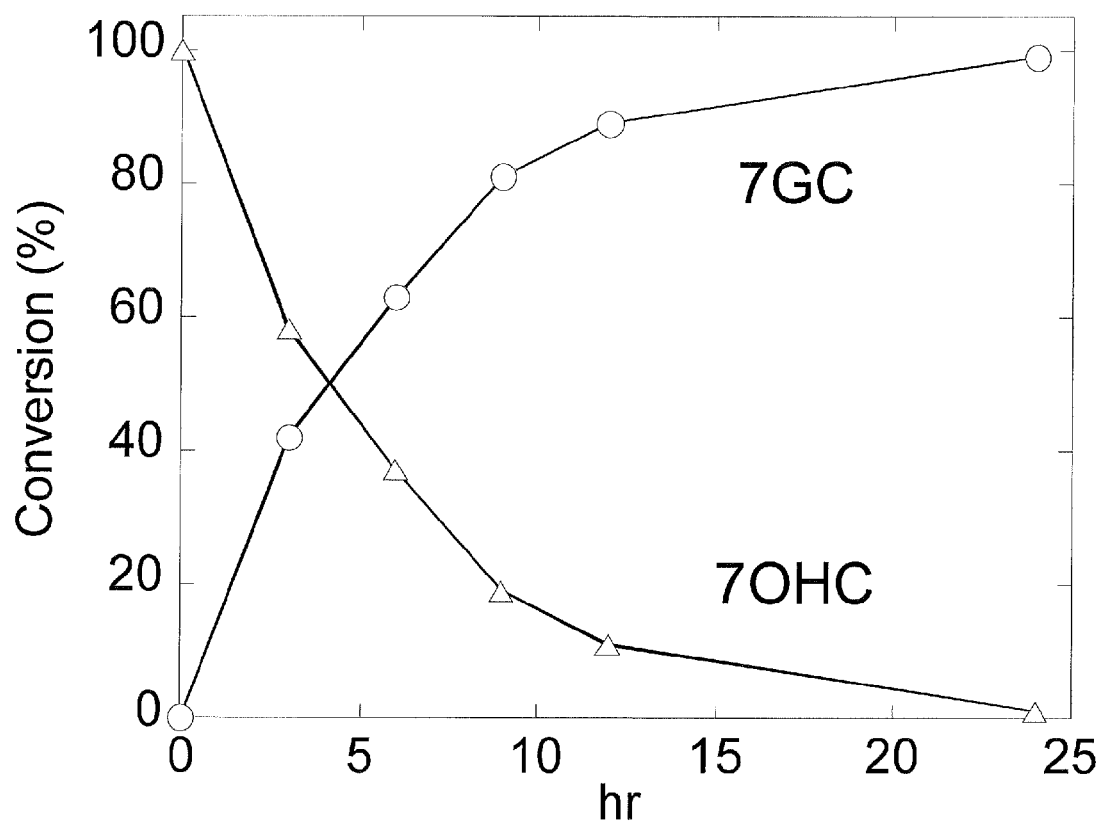
FIG. 6 shows the change over time in glucuronide production in UGT1A6 simultaneous expression strains.

FIG. 6 indicated time-dependent decrease of substrate (0.5 mM 7OHC: Δ) and increase of glucuronide (7GC: ○), resulting in the complete conversion of 7OHC to glucuronide after 24 hrs.

3-1-3. Effect of Concentration of Glucose on the Production of Glucuronide in UGT1A6 Co-Expression System Glucose concentration dependence of conversion in the transformant with the highest activity of glucuronidation (AH22: pAUR/At.UDPGDH+pGYR/hUGT1A6) was examined (FIG. 7).

Figure 7:
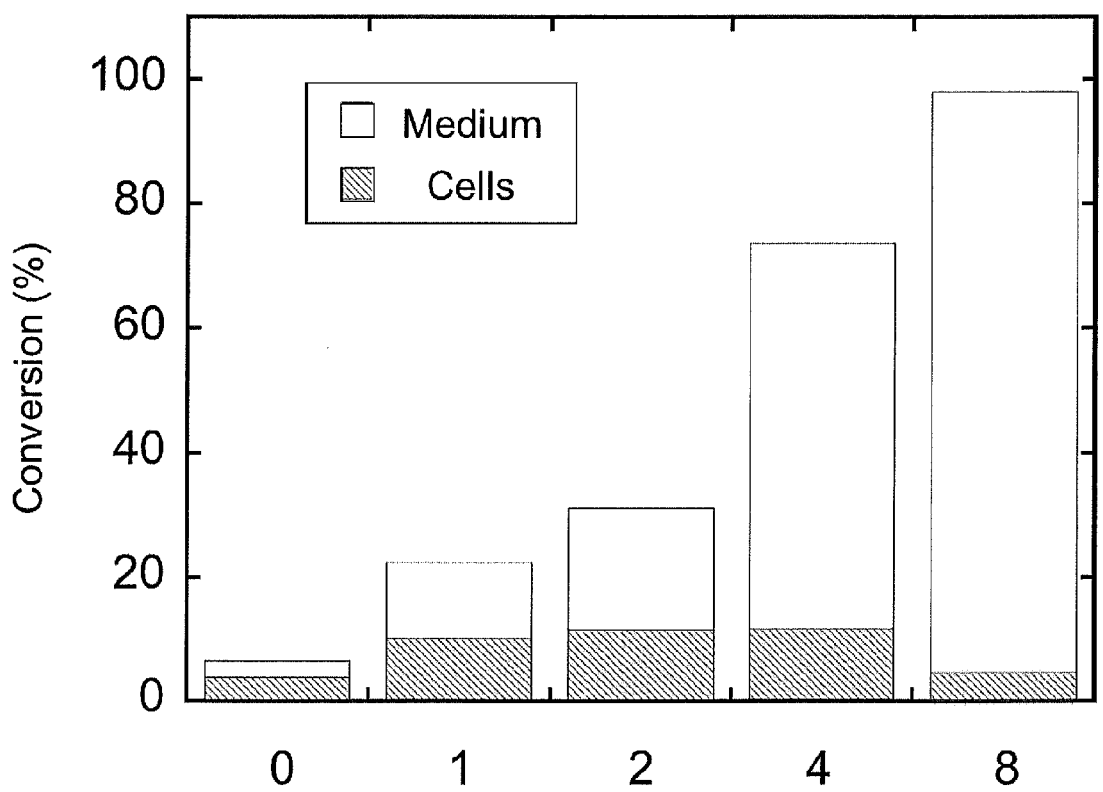
FIG. 7 shows the effect of glucose concentration on glucuronide production in UGT1A6 simultaneous expression strains.

FIG. 7 indicated concentration-dependent increase of glucuronide, resulting in the complete conversion of 7OHC to glucuronide at 8% (w/v) glucose. Base on the analysis of glucuronide in medium and cells, 90% of glucuronide were secreted out of the cells.

3-1-4. Effect of Combination of Expression Vectors on the Co-Expression

To examine the effect of combination of expression vectors on the production of glucuronide in yeast cells, co-expressed transformants (No. 1-4) as shown in Table 2 were cultivated with selection medium at 30° C., 48 hrs, and the resultant yeast cells were suspended with appropriate buffer solution containing 1 mM 7-hydroxycoumarine and 8% (w/v) glucose. After incubation at 30° C., 24 hrs, 2-fold volume of chloroform:methanol (3:1, v/v) was added to reaction medium containing yeast cells. Centrifugation of extracts was separated to upper water and lower organic phase. Upper water phase was analyzed by UPLC system (FIG. 8).

Figure 8:
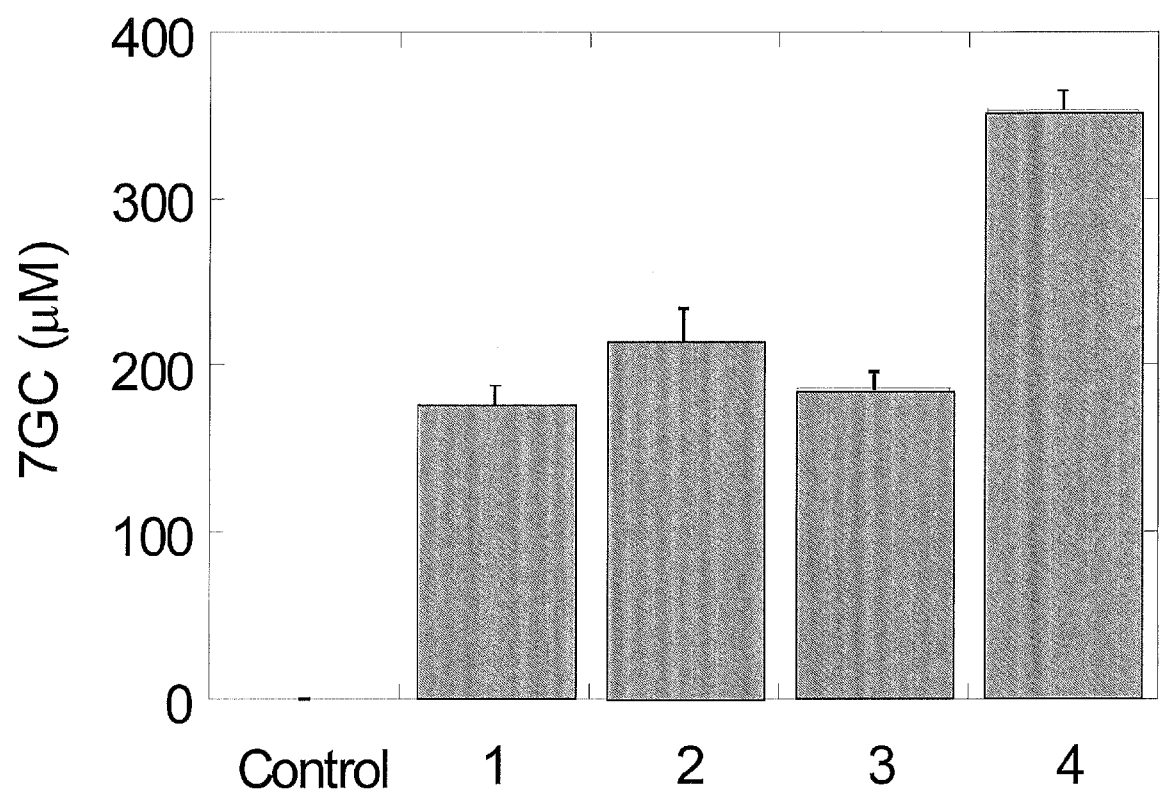
FIG. 8 shows the effect of expression vector combinations on the production of glucuronides by simultaneous expression strains.

The comparison of glucuronide formation in transformants (Nos. 1-3) of FIG. 8 indicated each transformant is independent on the combination of expression vectors. Results of No. 3 and No. 4 showed the comparable ability of yeast expressed UDPGDH derived from rat and plant to supply UDP-glucuronic acid for glucuronidation.

3-2. Production of Quercetin Glucuronide Using Resting Yeast Cells

To confirm the production of quercetin glucuronide in the resting yeast cells containing UDPGDH and UGT (pAUR/At.UDPGDH+pGYR/hUGT1A1), transformants were cultivated in selection medium at 30° C., 48 hrs, and the resultant yeast cells were suspended with 0.1 M potassium phosphate buffer (pH 7.4) containing 0.2 mM quercetin and 8% (w/v) glucose. After incubation at 30° C., 24 hrs, 2-fold volume of chloroform:methanol (3:1, v/v) was added to reaction medium containing yeast cells. Centrifugation of extracts was separated to upper water and lower organic phase. Lower organic phase were evaporated and redissolved in 200 μl acetonitrile. Quercetin glucuronides in yeast cells was isolated and detected by WAKOPAK™ Navi C30-5 (3 mm×150 mm, Wako Chemical)-column-HPLC system with followed condition; flow rate; 0.4 ml/min, detection; 370 nm, temperature 37° C. Condition of gradient elution: water-acetonitrile with 0.5% (v/v) phosphoric acid, 18% (v/v) acetonitrile (10 min), 18-55% acetonitrile (10 min), 55% acetonitrile (5 min).

Figure 9:
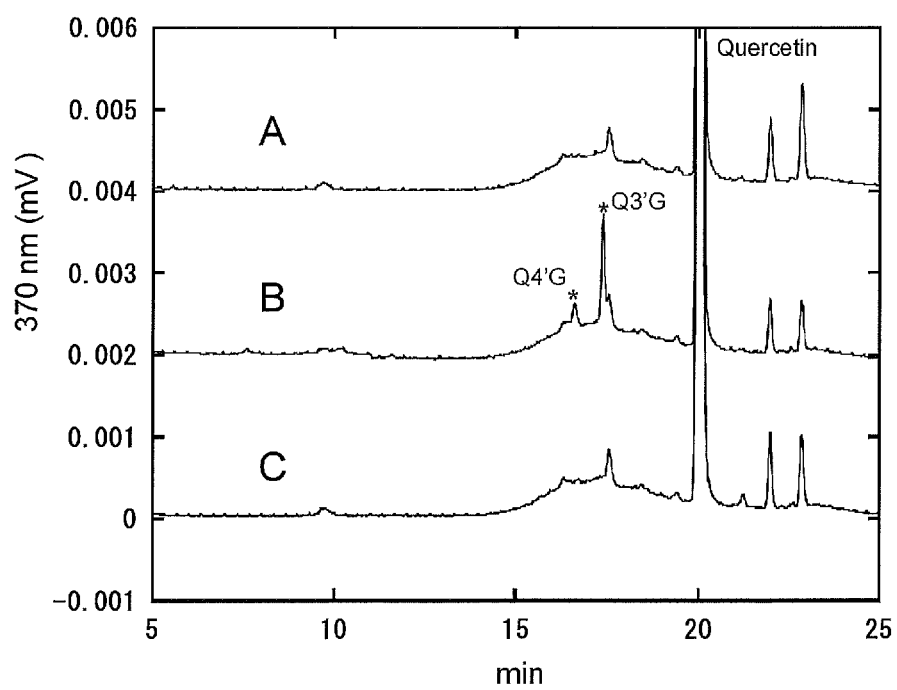
FIG. 9 shows the results of producing quercetin glucuronide using stationary yeast cells.

As shown in FIG. 9, the production of quercetin glucuronide was confirmed in the co-expressed transformant (pAUR/At.UDPGDH+pGYR/hUGT1A1).A:AH22:pGYR/UGT1A1, B:AH22/pGYRUGT1A1+pAUR/At.UDPGDH, C:AH22:pAUR/At.UDPGDH Quercetin is conjugated at multiple site of phenolic hydroxyl group. FIG. 9 indicated the preferential production of querecetin glucuronide at 3' phenolic hydroxyl group in B ring. The combination of UGT isoforms with UDPGDH could allow us to produce the regiospecific glucuronides of several compounds.

3-3. Production of Mycophenolic Acid Glucuronide Using Resting Yeast Cells

To confirm the production of mycophenolic acid glucuronide in the resting yeast cells containing UDPGDH and UGT(pAUR/At.UDPGDH+pGYR/hUGT1A9), transformants were cultivated in selection medium at 30° C., 48 hrs, and the resultant yeast cells were suspended with appropriate buffer solution containing 0.2 mM mycophenolic acid and 8% (w/v) glucose. After incubation at 30° C., 24 hrs, 2-fold volume of chloroform:methanol (3:1, v/v) was added to reaction medium containing yeast cells. Centrifugation of extracts was separated to upper water and lower organic phase. Lower organic phase were evaporated and redissolved in 200 μl acetonitrile. Each phase was analyzed by UPLC system. Condition of analysis are described below; column: Cosmosil 2.5C18-MS-II (2.0 mm×100 mm, nacalai tesque), flow rate 0.5 ml/min, detection 250 nm, temperature 45° C. Condition of gradient elution: water-acetonitrile with 0.1% (v/v) trifluoroacetic acid, 20-40% acetonitrile (7 min), 40% acetonitrile (2 min), 40-20% acetonitrile (2 min), 20% acetonitrile (2 min).

Figure 10:
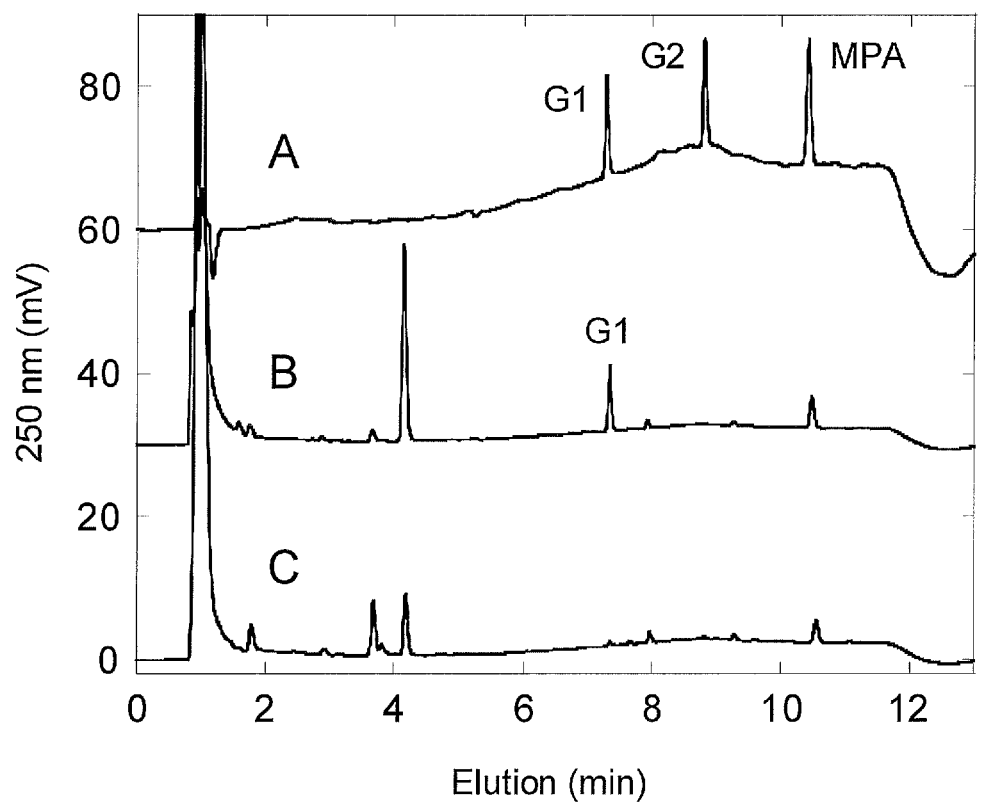
FIG. 10 shows the results of producing mycophenolic acid glucuronide using stationary yeast cells.

As shown in FIG. 10, the production of mycophenolic acid glucuronide was confirmed in the co-expressed transformat (pAUR/At.UDPGDH+pGYR/hUGT1A9). A: Standard compounds (MPA; mycophenolic acid, MPA-G1; mycophenolic-O-glucuronide, MPA-G2; mycophenolic acyl-glucuronide), B:AH22/pGYRUGT1A9+pAUR/At.UDPGDH, C:AH22: pAUR/At.UDPGDH Mycophenilic acid is conjugated at phenolic hydroxyl group and carboxyl group. FIG. 10 indicated the preferential production of mycophenolic-O-glucuronide at phenolic hydroxyl group in B ring. The combination of UGT isoforms with UDPGDH could allow us to produce the regiospecific glucuronides of several compounds.

3-4. Production of Acyl Glucuronide Using Resting Yeast Cells

To confirm the production of acyl glucuronide in the resting yeast cells containing UDPGDH and UGT, transformants were cultivated in selection medium at 30° C., 48 hrs, and the resultant yeast cells were suspended with appropriate buffer solution containing 1 mM mefenamic acid and 8% (w/v) glucose. After incubation at 30° C., 24 hrs, 2-fold volume of chloroform:methanol (3:1, v/v) was added to reaction medium containing yeast cells. Centrifugation of extracts was separated to upper water and lower organic phase. Lower organic phase were evaporated and redissolved in 200 μl acetonitrile. Each phase was analyzed by UPLC system. Condition of analysis are described below; column: Cosmosil 2.5C18-MS-II (2.0 mm×100 mm, nacalai tesque), flow rate 0.5 ml/min, detection 320 nm, temperature 45° C. Condition of gradient elution: water-acetonitrile with 0.1% (v/v) trifluoroacetic acid, 5-40% acetonitrile (5 min), 40-100% acetonitrile (3 min), 100% acetonitrile (1 min), 100-5% acetonitrile (3 min), 5% acetonitrile (3 min).

Figure 11:
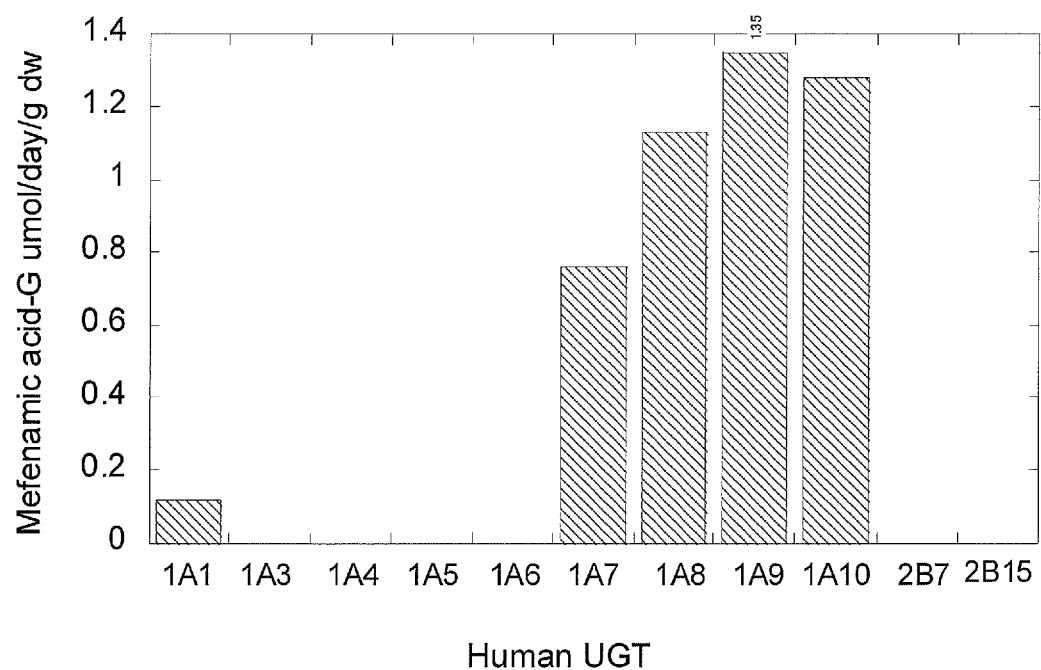
FIG. 11 shows the results of producing acyl glucuronides of mefenamic acid using stationary yeast cells.

FIG. 11 indicated the ratio of mefenamic acid acyl glucuronide production in resting yeast cells. Among human UGT, UGT1A8, 9, and 10 showed the significant activity of acyl glucuronide formation.

3-5. Production of N-Glucuronide Using Resting Yeast Cells

To confirm the production of N-glucuronide in the resting yeast cells containing UDPGDH and UGT (pAUR/At.UDPGDH+pGYR/hUGT1A4), transformants were cultivated in selection medium at 30° C., 48 hrs, and the resultant yeast cells were suspended with 0.1M potassium phosphate buffer (pH 7.4) containing 1 mM tamoxfen and 8% (w/v) glucose. After incubation at 30° C., 24 hrs, 2-fold volume of chloroform:methanol (3:1, v/v) was added to reaction medium containing yeast cells. Centrifugation of extracts was separated to upper water and lower organic phase. Lower organic phase were evaporated and redissolved in 200 μl acetonitrile. Quercetin glucuronides in yeast cells was isolated and detected by WAKOPAK™ Navi C30-5 (3 mm×150 mm, Wako Chemical)-column-HPLC system with followed condition; flow rate; 0.5 ml/min, detection; 254 nm, temperature 37° C. Condition of gradient elution: 100 mM ammonium acetate (pH 5.0)-acetonitrile, 25% (v/v) acetonitrile (5 min), 25-75% acetonitrile (25 min), 75% (v/v) acetonitrile (10 min), 75-25% acetonitrile (5 min), 25% acetonitrile (5 min).

Figure 12:
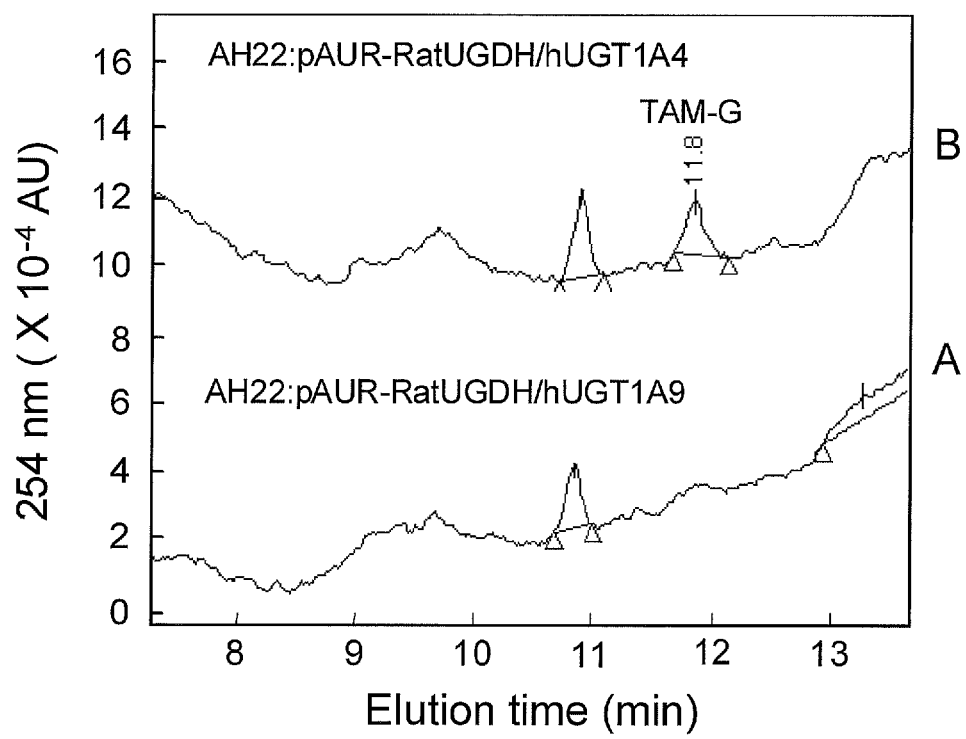
FIG. 12 shows the results of producing Tamoxifen glucuronide (N-glucuronide) using stationary yeast cells.

Tamoxifen is well-known to be anticancer drug with N-glucuronidation site. FIG. 12 indicated reverse phase HPLC elution pattern of production of tamoxifen N-glucuronide. The yeast transformant with UDPGDH and human UGT1A4 gene showed the production of N-glucuronide with elution time around 11.8 min.

Application 4
Comparison of Production of Glucuronide in Budding and Fission Yeast To compare the production ability of glucuronide in budding (Saccharomyces cerevisiae) and fission yeast (Schizosaccharomyces pombe) containing UDPGDH and UGT, several transformants (No. 4 in Table 2 and transformant with N-terminal modified UGT1A1) were selected for the assay. These transformants were cultivated in selection medium at 30° C., 48 hrs, and the resultant yeast cells were suspended with appropriate buffer solution containing 0.5 mM 4-methylumberrferone and 8% (w/v) glucose. After incubation at 30° C., 24 hrs, 2-fold volume of chloroform: methanol (3:1, v/v) was added to reaction medium containing yeast cells. Centrifugation of extracts was separated to upper water and lower organic phase. Lower organic phase were evaporated and redissolved in 200 μl acetonitrile. Each phase was analyzed by UPLC system.

Condition of analysis are described below; column: COSMOSIL™ 2.5C18-MS-II (2.0 mm×100 mm, Nacalai Tesque), flow rate 0.5 ml/min, detection 320 nm, temperature 45° C. Condition of gradient elution: water-acetonitrile with 0.1% (v/v) trifluoroacetic acid, 10% acetonitrile (4 min), 10-70% acetonitrile (6 min), 70-10% acetonitrile (2 min), 10% acetonitrile (3 min).

Table 6 showed the comparison of production of 4-methylumberrferone glucuronide in budding and fission yeast. The production ratio of glucuronide in budding yeast with UGT1A1 and UGT1A6 are 10- and 50-higher than those in fission yeast, respectively. The amount of glucuronide per dry weight of budding yeast indicated 20 to 100-fold increase compare to fission yeast. In the several cases of UGT isoforms, these results showed the advantage of budding yeast in the production of glucuronide.

[Table 6]

TABLE 6

Comparison of production of 4-metylumberrferone glucuronide in budding and fission yeast

| | μM/day | | moL/day/g biomass dry weight | |
| --- | --- | --- | --- | --- |
| UGT | budding | fission[a] | budding | fission[a] |
| UGT1A1 | 20.2 | 1.8 | 2.6 | 0.14 |
| UGT1A6 | 195.7 | 3.5 | 24.8 | 0.22 |

[a]Glucuronide production by whole-cell biotransformation using genetically engineered fission yeast S. pombe.
Dragan C A, Buchheit D, Bischoff D, Ebner T, Bureik M.
Drug Metab Dispos.. [Epub ahead of print]PMID: 20008039 [PubMed - as supplied by publisher]

Application 5
5-1. The Production of 7-Hydroxycoumarine Glucuronide in Resting Yeast Cells with Co-Expression System Containing UDPGDH, UGT, and Cytochrome P450

In the precursor of most glucuronide, hydroxyl groups are introduced by P450-dependent monooxynenation. To analyze the structure and function of these xenobiotic metabolizing enzymes the expression system of several mammalian P450 and UGT isoforms was constructed in budding yeast cells, *Saccharomyces cerevisiae* AH22. This in vitro system is able to convert 7-ethoxycoumarine to its glucuronide via hydroxyl intermediate, 7-hydroxycoumarine (Ref 6). Yeast cells lack the ability of production of UDP-glucuronic acid (UDP-GlcUA) from UDP-glucose to synthesize the glucuronide in whole cells. To achieve the sequential production of hydroxyl intermediate and glucuronidation, co-expression yeast system containing UDPGDH, UGT, and P450 was constructed using combination of expression vectors (pAUR-At.UDPGDH/UGT1A6 and pGYR/ratCYP1A1, No. 5 in Table 2). These transformants were cultivated in selection medium at 30° C., 48 hrs, and the resultant yeast cells were suspended with appropriate buffer solution containing 1 mM 7-ethoxycoumarine and 8% (w/v) glucose. After incubation at 30° C., 72 hrs, 2-fold volume of chloroform:methanol (3:1, v/v) was added to reaction medium containing yeast cells. Centrifugation of extracts was separated to upper water and lower organic phase. Lower organic phase were evaporated and redissolved in 200 µl acetonitrile. Each phase was analyzed by UPLC system (FIG. 13).

Figure 13:
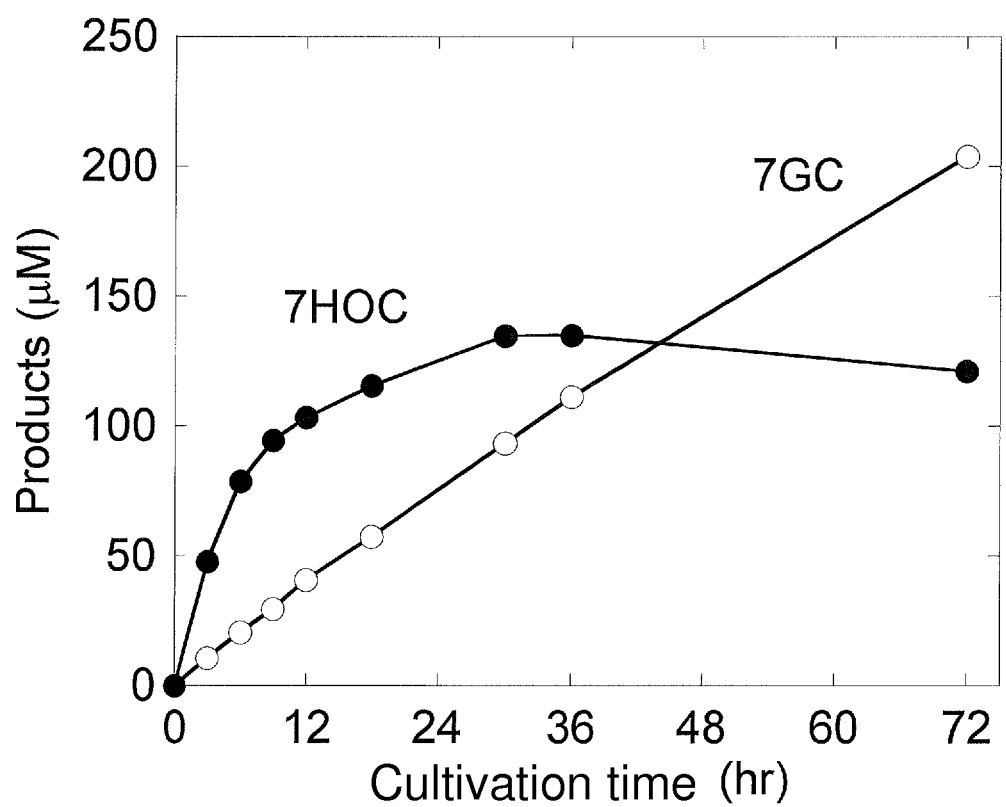
FIG. 13 shows the results of producing 7-hydroxycoumarin glucuronide using the stationary cells of simultaneous expression strains containing cytochrome P450.

As indicated in FIG. 13, 7-ethoxycoumarine was deethylated by P4501A1 and the resultant 7-hydroxycoumarine (●) was glucuronidated by UGT1A6 to its glucuronide (○). The formation of glucuronide has no lag phase, suggesting the sequential conversion of P450-UGT-dependent reaction with NADPH and UDP-glucuronic acid. Thus, this yeast co-expression system containing UDPGDH, UGT, and P450 allow us to produce the glucuronide from the parent compounds efficiently.

5-2. Production of 7-Hydroxycoumarine and Glucuronide from 7-Ethoxycoumarine Using Resting Yeast Cells Containing UDPGDH, UGT, and Human P450

As shown in application 3, many drugs are metabolized by P450, followed by the glucuronide formation. To produce the drug metabolites, co-expression system containing human P450 was constructed and the metabolism of 7-ethoxycoumarine was analyzed.

5-2-1. Construction of Expression Vector Containing Human P450 (pPYR)

Figure 14:
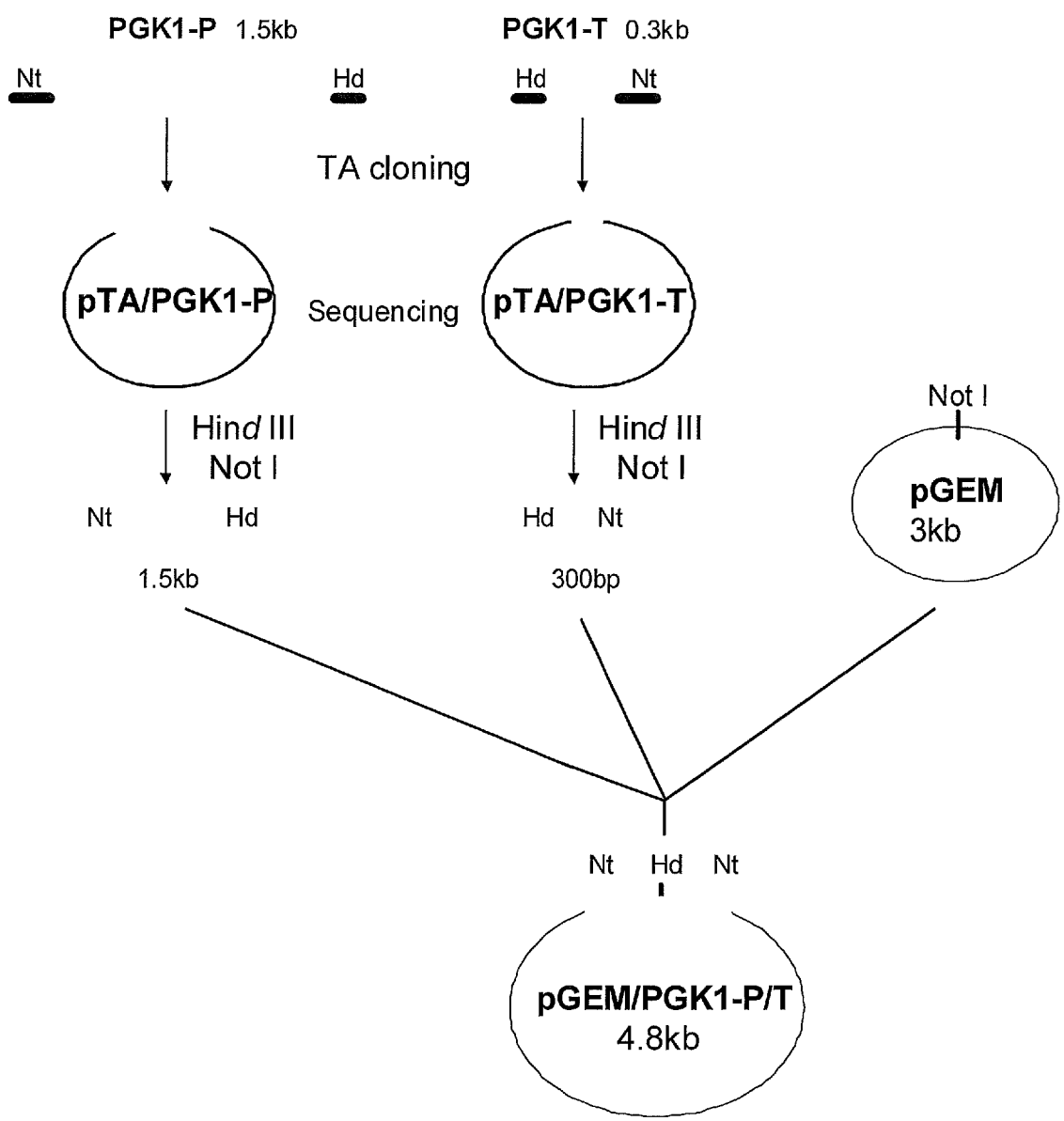
FIG. 14 shows the construction scheme of human cytochrome P450 expression plasmid having an *S. cerevisiae* PGK1-derived promoter and terminator regions.
Figure 14:
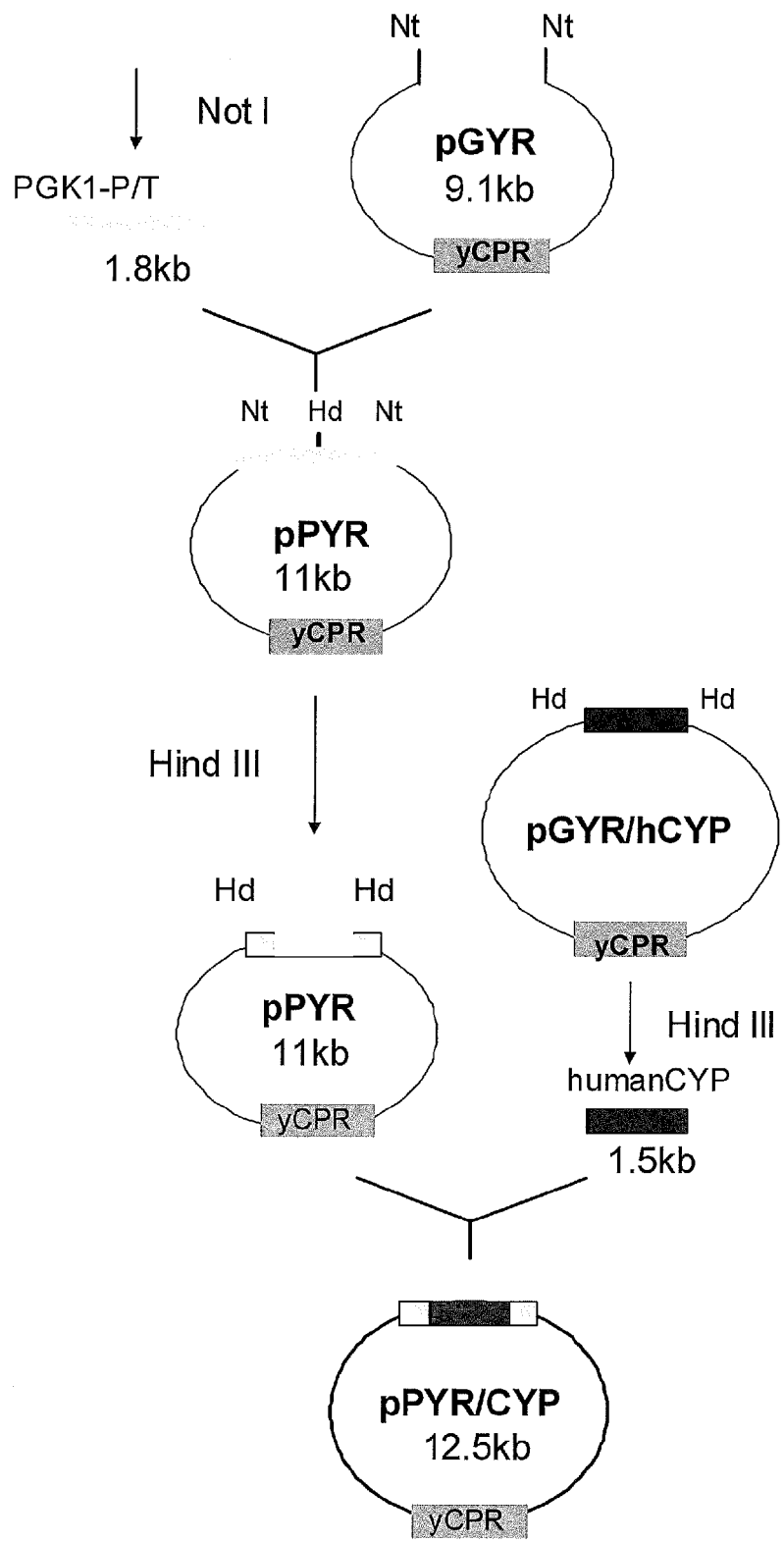

To construct the co-expression system containing human P450, promoter and terminator region of phosphoglycerol kinase (PGK1) derived from budding yeast was cloned and multicopy plasmid with promoter and terminator region of PGK1 was constructed for yeast expression (FIG. 14).

Genome DNA was prepared from AH22 (*Saccharomyces cerevisiae*) using conventional method. The PCR cloning of promoter and terminator region of PGK1 was performed using genome DNA as template and a set of specific primers.

KOD-plus-(TOYOBO™) was used as DNA polymerase. PCR amplification was performed in reaction condition and specific primers as described below;
For promoter region of PGK1
Forward primer: SEQ. ID NO: 21
Reverse primer: SEQ. ID NO: 22
For terminator region of PGK1
Forward primer: SEQ. ID NO: 23
Reverse primer: SEQ. ID NO: 24

```
                                                SEQ. ID NO: 21
              TTGCGGCCGCTCTAACTGATCTATCCAAAA

SEQ. ID NO: 22
              CCCAAGCTTTGTTTTATATTTGTTGTAAA

SEQ. ID NO: 23
              CCCAAGCTTATTGAATTGAATTGAAATCG

SEQ. ID NO: 24
              TTGCGGCCGCTAACGAACGCAGAATTTT
```

PCR condition
Denature 94° C. 2 min
5 cycles 94° C. 15 sec, 37° C. 30 sec, 68° C. 1 min 45 sec
30 cycles 94° C. 15 sec, 55° C. 30 sec, 68° C. 1 min45 sec
Extension 68° C. 10 min Analysis of PCR products using agarose gel electrophoresis resulted in the specific amplification of DNA fragments with 1.5 kb and 0.3 kbp of promoter and terminator sequence, respectively. After the PCR fragments of reaction mixture were separated, the purified fragments were cloned to pTA vector using TARGET CLONE™-plus-(TOYOBO™). The DNA sequence analysis of the resultant clones confirmed the gene products from Genbank Acc. No. BK006937, TPA: *Saccharomyces cerevisiae* S288c chromosome III, complete sequence; 136264-137743 and Genbank Acc. No. BK006937, TPA: *Saccharomyces cerevisiae* S288c chromosome III, complete sequence; 138995-139270, as showed in SEQ. ID NO: 25 and 26, respectively.

```
SEQ. ID NO: 25:
TCTAACTGATCTATCCAAAACTGAAAATTACATTCTTGATTAGGTTTATCACAGGCAAATG

TAATTTGTGGTATTTTGCCGTTCAAAATCTGTAGAATTTTCTCATTGGTCACATTACAACC

TGAAAATACTTTATCTACAATCATACCATTCTTATAACATGTCCCCTTAATACTAGGATCAG

GCATGAACGCATCACAGACAAAATCTTCTTGACAAACGTCACAATTGATCCCTCCCCAT

CCGTTATCACAATGACAGGTGTCATTTTGTGCTCTTATGGGACGATCCTTATTACCGCTT

TCATCCGGTGATAGACCGCCACAGAGGGGCAGAGAGCAATCATCACCTGCAAACCCTT

CTATACACTCACATCTACCAGTGTACGAATTGCATTCAGAAAACTGTTTGCATTCAAAAA

TAGGTAGCATACAATTAAAACATGGCGGGCATGTATCATTGCCCTTATCTTGTGCAGTTA

GACGCGAATTTTTCGAAGAAGTACCTTCAAAGAATGGGGTCTTATCTTGTTTTGCAAGT

ACCACTGAGCAGGATAATAATAGAAATGATAATATACTATAGTAGAGATAACGTCGATGAC
```

-continued

```
TTCCCATACTGTAATTGCTTTTAGTTGTGTATTTTTAGTGTGCAAGTTTCTGTAAATCGAT

TAATTTTTTTTTCTTTCCTCTTTTTATTAACCTTAATTTTTATTTTAGATTCCTGACTTCAAC

TCAAGACGCACAGATATTATAACATCTGCATAATAGGCATTTGCAAGAATTACTCGTGAG

TAAGGAAAGAGTGAGGAACTATCGCATACCTGCATTTAAAGATGCCGATTTGGGCGCG

AATCCTTTATTTTGGCTTCACCCTCATACTATTATCAGGGCCAGAAAAAGGAAGTGTTTC

CCTCCTTCTTGAATTGATGTTACCCTCATAAAGCACGTGGCCTCTTATCGAGAAAGAAAT

TACCGTCGCTCGTGATTTGTTTGCAAAAAGAACAAAACTGAAAAAACCCAGACACGCT

CGACTTCCTGTCTTCCTATTGATTGCAGCTTCCAATTTCGTCACACAACAAGGTCCTAG

CGACGGCTCACAGGTTTTGTAACAAGCAATCGAAGGTTCTGGAATGGCGGGAAAGGG

TTTAGTACCACATGCTATGATGCCCACTGTGATCTCCAGAGCAAAGTTCGTTCGATCGT

ACTGTTACTCTCTCTTTCAAACAGAATTGTCCGAATCGTGTGACAACAACAGCCTGT

TCTCACACACTCTTTTCTTCTAACCAAGGGGGTGGTTTAGTTTAGTAGAACCTCGTGAA

ACTTACATTTACATATATATAAACTTGCATAAATTGGTCAATGCAAGAAATACATATTTGGT

CTTTTCTAATTCGTAGTTTTTCAAGTTCTTAGATGCTTTCTTTTTCTCTTTTTTACAGATCA

TCAAGGAAGTAATTATCTACTTTTTACAACAAATATAAAACA

SEQ. ID NO: 26:
ATTGAATTGAATTGAAATCGATAGATCAATTTTTTTCTTTTCTCTTTCCCCATCCTTTACG

CTAAAATAATAGTTTATTTTATTTTTTGAATATTTTTTATTTATATACGTATATATAGACTATTA

TTTATCTTTTAATGATTATTAAGATTTTTATTAAAAAAAAATTCGCTCCTCTTTTAATGCCTT

TATGCAGTTTTTTTTCCCATTCGATATTTCTATGTTCGGGTTCAGCGTATTTTAAGTTTAA

TAACTCGAAAATTCTGCGTTCGTTA
```

After the digest of plasmids containing PGK1 promoter or terminator using Not I and Hind III at 37° C., the resultant fragment of the genes were separated using agarose gel electrophoresis and WIZARD™ SV Gel and PCR Clean-Up System (PROMEGA™).

After the digest of PGEM™-T-Easy Vector (PROMEGA™) as subcloning vector using Not I at 37° C., the resultant fragment of the genes (ca 3 kbp) were separated using agarose gel electrophoresis and WIZARD™ SV Gel and PCR Clean-Up System (PROMEGA™).

After estimation of DNA concentration of two kind of insert and pGEM vector using agarose gel electrophoresis, mixture of each gene at 3:1 to 10:1 molecules was ligated at 16° C., 1 hr using DNA Ligation Kit Ver. 2 (TAKARA™). After the ligation reaction, E. coli JM109 transform with the reaction mixture and spread on LB agarose plate with 50 µg/ml ampicillin. To select the transformed colonies, direct PCR amplification were performed as colonies. EX TAQ™ (TAKARA™) was used as DNA polymerase. Forward primer (SEQ. ID NO: 21) and reverse primers (SEQ. ID NO: 24) were used. PCR amplification was performed in reaction condition and specific primers as described below;

PCR condition
Denature 98° C. 5 min
30 cycles 94° C. 30 sec, 50° C. 30 sec, 72° C. 2 min 30 sec
Extension 72° C. 4 min After analysis of colony PCR, several clones with the desirable PCR amplification (ca 1.8 kbp) were obtained from LB plate. The resultant clones were cultivated with 5 ml LB medium with 50 µg/ml ampicillin at 37° C., 200 rpm, and 16 hrs. Each plasmid was purified from the cultures using alkaline-SDS method. Digest of plasmids with Not I and Hind III confirmed the construction of the vectors containing PGK1 promoter or terminator with Hind III at cloning site (pGEM/PGK-1-P/T)

After the digest of plasmids containing PGK1 promoter and terminator using Not I at 37° C., the resultant fragment of the genes were separated using agarose gel electrophoresis and WIZARD™ SV Gel and PCR Clean-Up System (PROMEGA™).

After the digest of pGYR as yeast expression vector using Not I at 37° C., the resultant fragment of the genes (ca 9 kbp) were separated using agarose gel electrophoresis and WIZARD™ SV Gel and PCR Clean-Up System (PROMEGA™).

After estimation of DNA concentration of insert and pGEM-Not I vector using agarose gel electrophoresis, mixture of each gene at 3:1 to 10:1 molecules was ligated at 16° C., 1 hr using DNA Ligation Kit Ver. 2 (TAKARA™). After the ligation reaction, E. coli JM109 was transformed with the reaction mixture and spread on LB agarose plate with 50 µg/ml ampicillin. To select the transformed colonies, direct PCR amplification were performed as colonies. EX TAQ™ (TAKARA™) was used as DNA polymerase. Forward primer (SEQ. ID NO: 21) and reverse primers (SEQ. ID NO: 24) were used. PCR amplification was performed in reaction condition and specific primers as described below;

PCR condition
Denature 98° C. 5 min
30 cycles 94° C. 30 sec, 50° C. 30 sec, 72° C. 2 min 30 sec
Extension 72° C. 4 min After analysis of colony PCR, several clones with the desirable PCR amplification (ca 1.8 kbp) were obtained from LB plate. The resultant clones were cultivated with 5 ml LB medium with 50 µg/ml ampicillin at 37° C., 200 rpm, and 16 hrs. Each plasmid was purified from the cultures using alkaline-SDS method. Digest of plasmids with Not I and Hind III confirmed the construction of the yeast expression vectors with PGK1 promoter and terminator sequence (pPYR).

After the digest of plasmid containing human P450 using Hind III at 37° C., 4 hrs, the resultant fragment of the genes (ca 11 kbp) were separated using agarose gel electrophoresis and WIZARD™ SV Gel and PCR Clean-Up System (PROMEGA™).

After the digest of pPYR as yeast expression vector using Hind III at 37° C., the resultant fragment of the genes (ca 11 kbp) were separated using agarose gel electrophoresis and WIZARD™ SV Gel and PCR Clean-Up System (PROMEGA™).

After estimation of DNA concentration of insert of human P450 cDNA and pPYR-Not I vector using agarose gel electrophoresis, mixture of each gene at 3:1 to 10:1 molecules was ligated at 16° C., 1 hr using DNA Ligation Kit Ver. 2 (TAKARA™). After the ligation reaction, E. coli JM109 was transformed with the reaction mixture and spread on LB agarose plate with 50 µg/ml ampicillin. To select the transformed colonies, direct PCR amplification were performed as colonies. EX TAQ™ (TAKARA™) was used as DNA polymerase. Forward primer (SEQ. ID NO: 21) and reverse primers of human P450 were used. PCR amplification was performed in reaction condition and specific primers as described below;

PCR condition
Denature 98° C. 5 min
30 cycles 94° C. 30 sec, 50° C. 30 sec, 72° C. 2 min 30 sec
Extension 72° C. 4 min After analysis of colony PCR, several clones with the desirable PCR amplification were obtained from LB plate. The resultant clones were cultivated with 5 ml LB medium with 50 µg/ml ampicillin at 37° C., 200 rpm, and 16 hrs. Each plasmid was purified from the cultures using alkaline-SDS method. Digest of plasmids with Not I and Hind III confirmed the construction of the yeast expression vectors of human P450 with PGK1 promoter and terminator sequence (pPYR/CYP).

5-2-2. Production of 7-Hydroxycoumarine and Glucuronide from 7-Ethoxycoumarine Using Resting Yeast Cells Containing UDPGDH, UGT, and Human P450

To achieve the sequential production of hydroxyl intermediate and glucuronidation, co-expression yeast system containing UDPGDH, UGT, and P450 was constructed using combination of expression vectors (pAUR-ratUDPGDH/UGT1A6 and pPYR/humanCYP).

These transformants were cultivated in selection medium at 30° C., 48 hrs, and the resultant yeast cells were suspended with appropriate buffer solution containing 1 mM 7-ethoxycoumarine and 8% (w/v) glucose. After incubation at 30° C., 72 hrs, 2-fold volume of chloroform:methanol (3:1, v/v) was added to reaction medium containing yeast cells. Centrifugation of extracts was separated to upper water and lower organic phase. Lower organic phase were evaporated and redissolved in 200 µl acetonitrile. Each phase was analyzed by UPLC system (FIG. 15 and Table 7).

TABLE 7

| | | UGT | | | | | |
|---|---|---|---|---|---|---|---|
| | | 1A1 | 1A6 | 1A7 | 1A8 | 1A9 | 2B7 |
| | | Glucuronide of 7-ethoxycoumarine | | | | | |
| CYP | 1A2 | | + | + | − | + | − |
| | 2D6 | | | + | + | | − |
| | 2C9 | | + | + | | − | − |
| | 2C19 | − | ++ | + | | + | − |
| | 3A4 | | ++ | + | − | − | |
| | | Glucuronide of 3-hydroxy-7-ethoxycoumarine | | | | | |
| CYP | 1A2 | | + | ++ | + | + | + |
| | 2D6 | | | +++ | +++ | | + |
| | 2C9 | | − | + | | + | + |
| | 2C19 | ++ | + | + | | ++ | + |
| | 3A4 | | + | + | + | ++ | |

Figure 15:
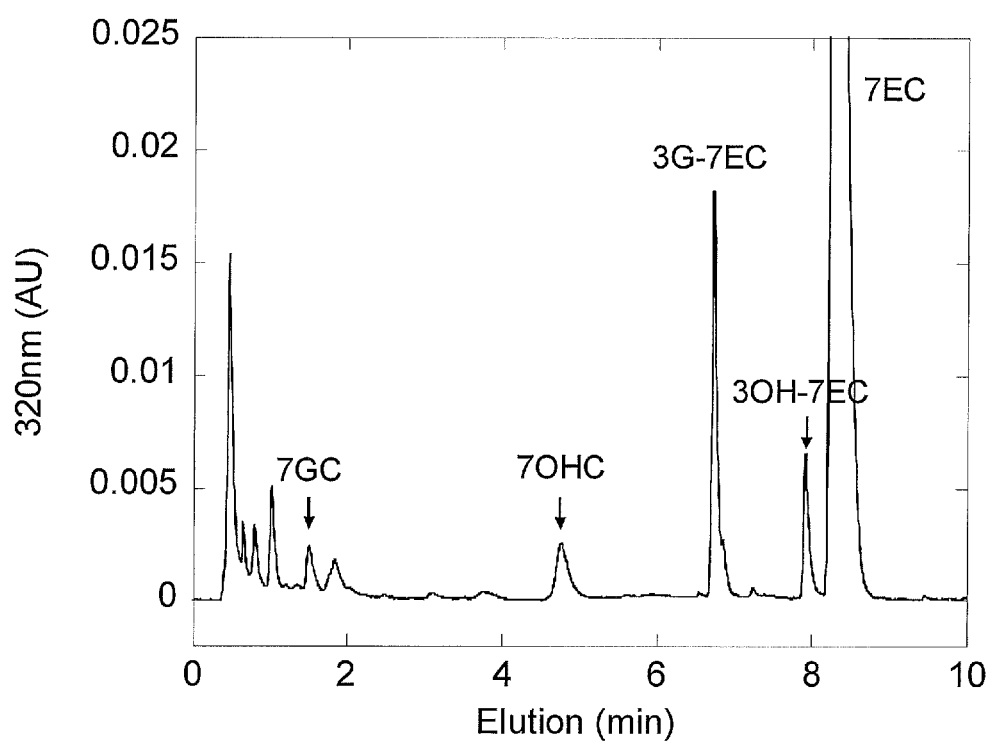
FIG. 15 shows the results of producing 7-ethoxycoumarin metabolites employing stationary cells of a yeast strain simultaneously expressing human cytochrome P450 (CYP2D6) and UDP-glucuronosyl transferase (UGT1A8).

FIG. 15 indicated reverse phase HPLC elution pattern of metabolites from 7-ethoxycoumarine using resting yeast cells containing UDPGDH, human UGT1A8, and human P450 2D6. 7-ethoxycoumarine was metabolized to 7-hydroxycoumarine or 3-hydroxy-7-ethoxycoumarine by human P450 2D6. Each hydroxyl intermediates further were metabolized to corresponding glucuronides by human UGT1A8.

Table 7 indicated the metabolism of 7-ethoxycoumarine using the yeast co-expression system with different combination of human UGT and P450 isoforms. The production of glucuronides from P450-dependent metabolites was observed in all transformants.

INDUSTRIAL APPLICABILITY

The present invention is useful in fields relating to analysis of drug metabolism in a human body in drug developments.

The invention claimed is:

1. A method for producing a glucuronide, comprising culturing a transformed *Saccharomyces cerevisiae* that has been transformed by the insertion in an expressible manner of a gene coding for UDP-glucose dehydrogenase from *Arabidopsis* or rat and a gene coding for UDP-glucuronosyl transferase from a mammal in the presence of glucose and a substance being glucuronided to cause a glucuronide of the substance being glucuronided to be produced; and collecting the produced glucuronide in culture medium.

2. The producing method according to claim 1, wherein the substance being glucuronided is at least one member selected from the group consisting of pharmaceuticals containing alcohol hydroxyl groups, candidate substances for such pharmaceuticals, polyphenol compounds comprising multiple phenol hydroxyl groups, non-steroidal anti-inflammatory drugs containing carboxylic acids, and candidate substances for such drugs.

3. The producing method according to claim 1, wherein the substance being glucuronided is a substance producing a functional group that undergoes glucuronidation when metabolized by P450.

4. The producing method according to claim 3 wherein the substance being glucuronided is at least one member selected from the group consisting of pharmaceuticals comprising methoxy groups or ethoxy groups, candidate substances for such pharmaceuticals, sesamin compounds having methylene dioxyphenyl groups, diazepine pharmaceuticals not comprising hydroxyl groups, and candidate substances for such pharmaceuticals.

5. The producing method according to claim 3, wherein the functional group is a hydroxyl group.

6. The producing method according to claim 1, wherein the transformed *Saccharomyces cerevisiae* has been further transformed by inserting in an expressible manner a human gene coding for cytochrome P450.

7. The producing method according to claim 1, wherein the gene coding for UDP-glycuronosyl transferase from a mammal is a human or pig gene coding for UDP-glucuronosyl transferase.

* * * * *